(12) United States Patent
Soule et al.

(10) Patent No.: US 9,970,014 B2
(45) Date of Patent: May 15, 2018

(54) FACTOR V/VA-TARGETING APTAMER COMPOSITIONS AND METHODS OF USING THE SAME

(71) Applicant: Duke University, Durham, NC (US)

(72) Inventors: Erin Soule, Durham, NC (US); Bruce A. Sullenger, Durham, NC (US)

(73) Assignee: Duke University, Durham, NC (US)

( * ) Notice: Subject to any disclaimer, the term of this patent is extended or adjusted under 35 U.S.C. 154(b) by 0 days. days.

(21) Appl. No.: 15/620,143

(22) Filed: Jun. 12, 2017

(65) Prior Publication Data

US 2017/0355992 A1    Dec. 14, 2017

Related U.S. Application Data

(60) Provisional application No. 62/348,198, filed on Jun. 10, 2016.

(51) Int. Cl.
| | | |
|---|---|---|
| C07H 21/02 | (2006.01) | |
| C07H 21/04 | (2006.01) | |
| C12N 15/115 | (2010.01) | |
| C12N 15/113 | (2010.01) | |
| C12N 5/00 | (2006.01) | |

(52) U.S. Cl.
CPC .......... *C12N 15/115* (2013.01); *C12N 15/113* (2013.01); *C12N 2310/113* (2013.01); *C12N 2310/16* (2013.01); *C12N 2310/322* (2013.01); *C12N 2310/3517* (2013.01); *C12N 2310/531* (2013.01); *C12N 2320/30* (2013.01); *C12N 2320/50* (2013.01)

(58) Field of Classification Search
None
See application file for complete search history.

*Primary Examiner* — Sean McGarry
(74) *Attorney, Agent, or Firm* — Andrus Intellectual Property Law, LLP

(57) ABSTRACT

Provided herein are Factor V/Factor Va-targeting aptamer compositions and antidote compositions targeting such aptamer compositions. Methods for preventing blood clots using such compositions are also provided.

20 Claims, 26 Drawing Sheets

Figure 10
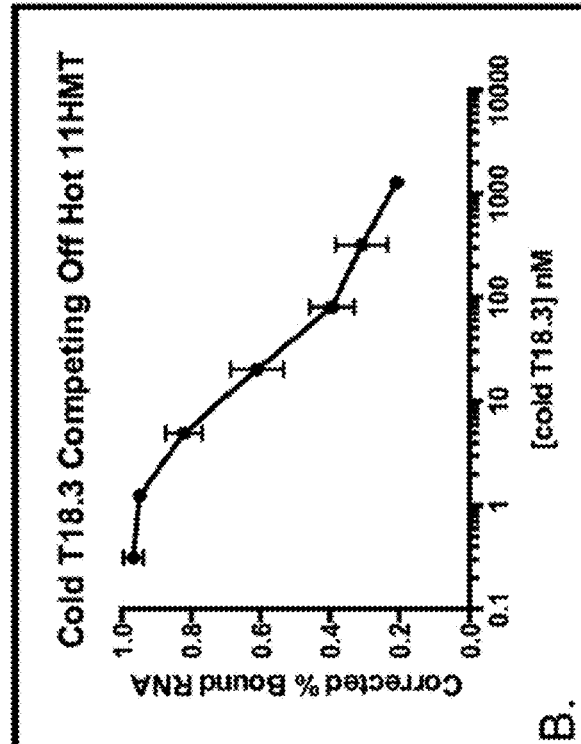
Fig. 10B
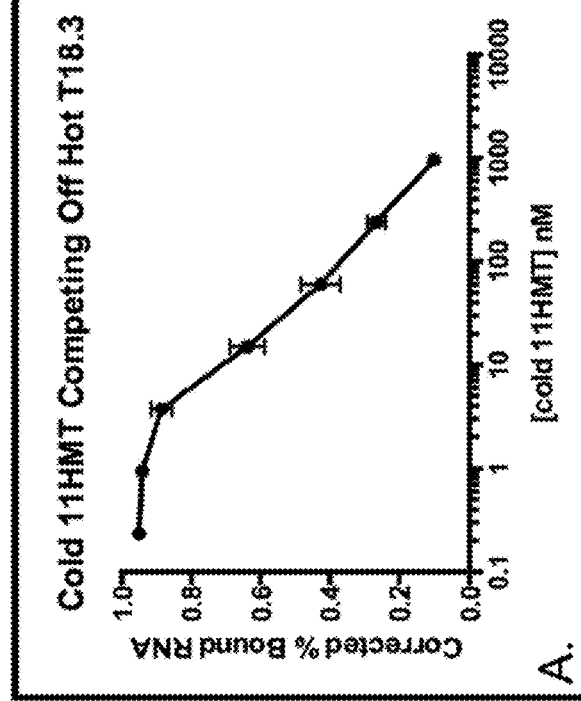
Fig. 10A

Figure 12
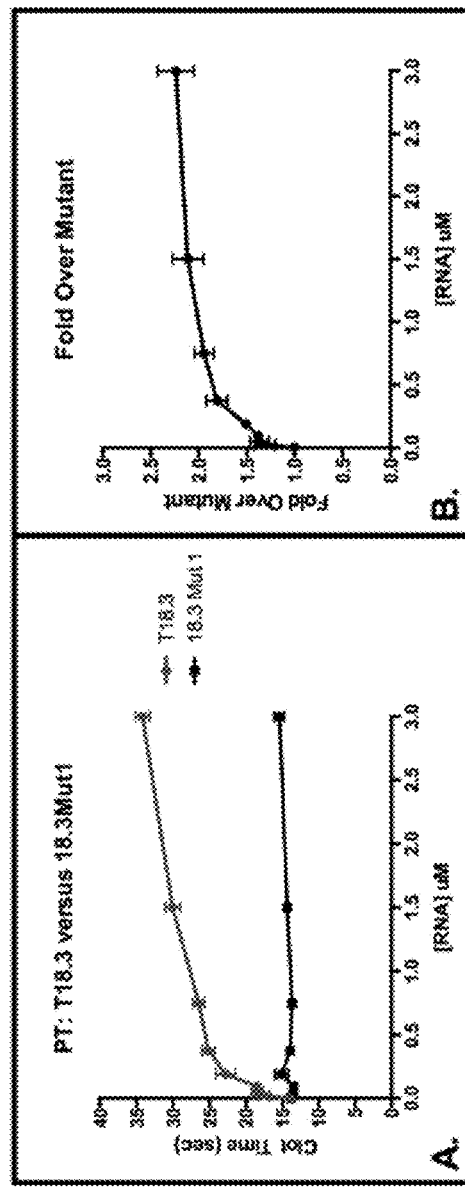
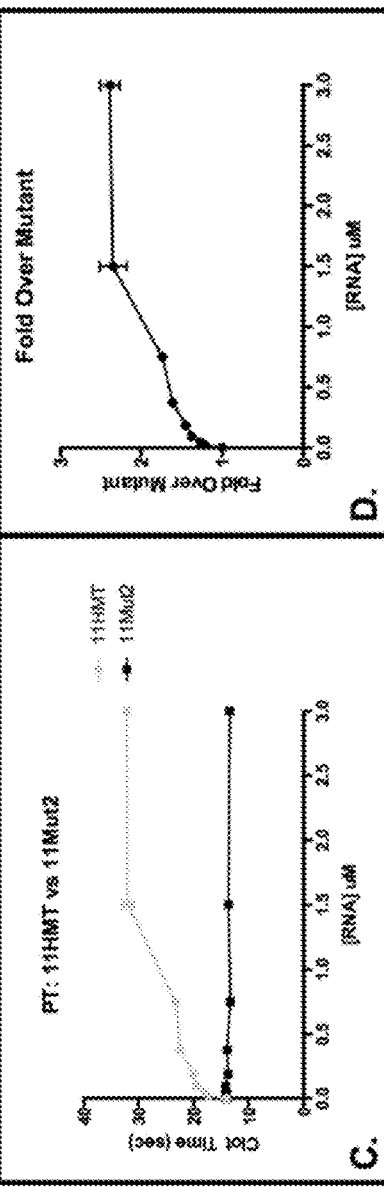
Fig. 12A
Fig. 12B
Fig. 12C
Fig. 12D

Figures 14A-D
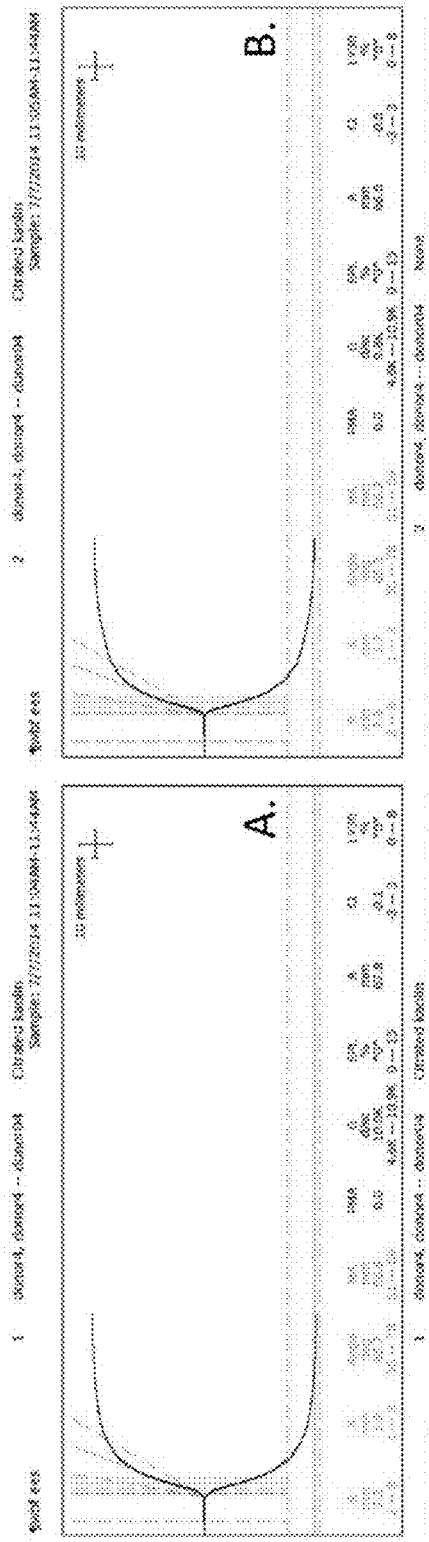
Fig. 14A
Fig. 14B
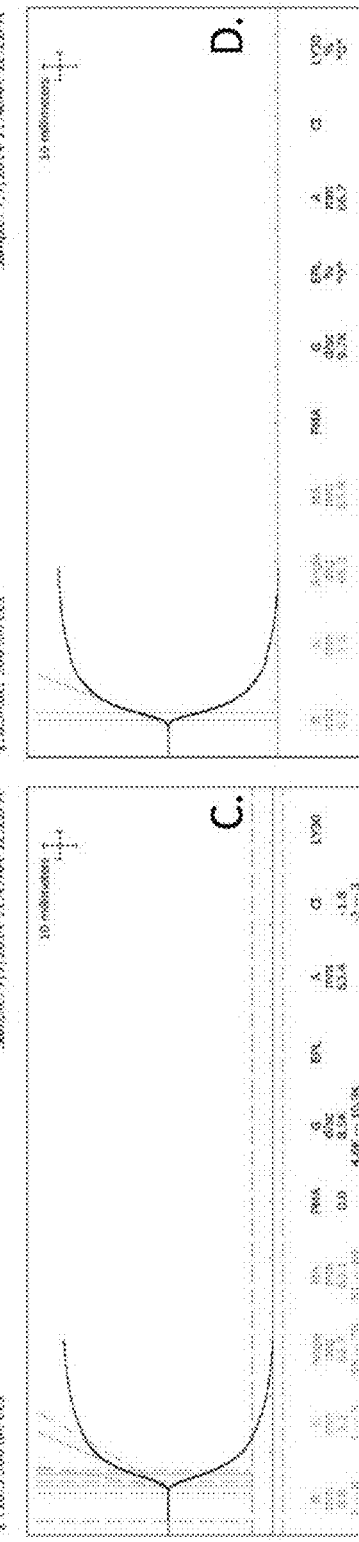
Fig. 14C
Fig. 14D

Figures 14E-H
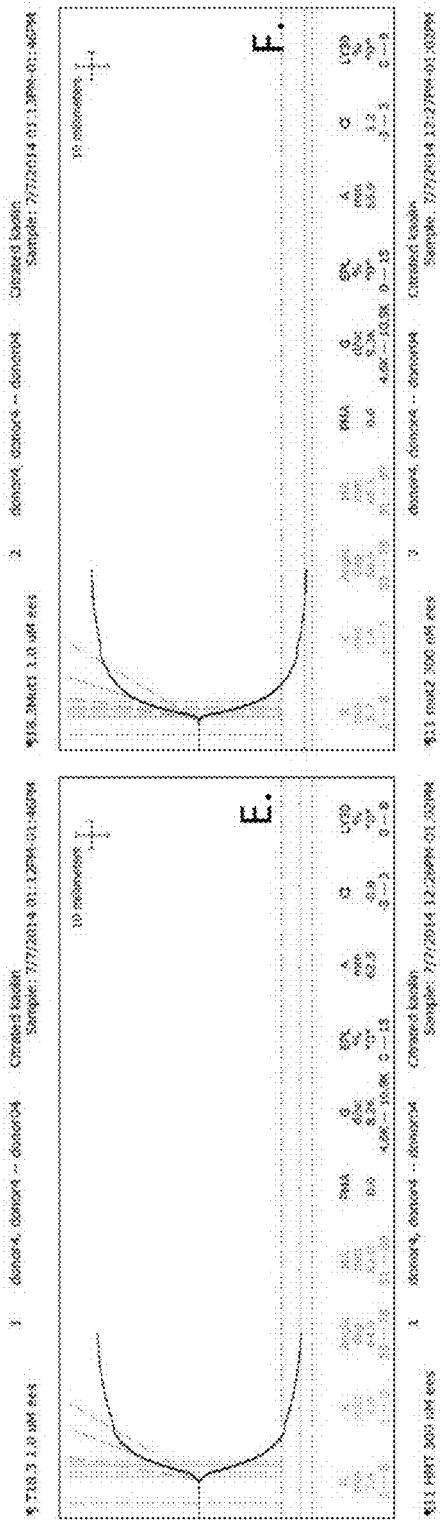
Fig. 14E
Fig. 14F
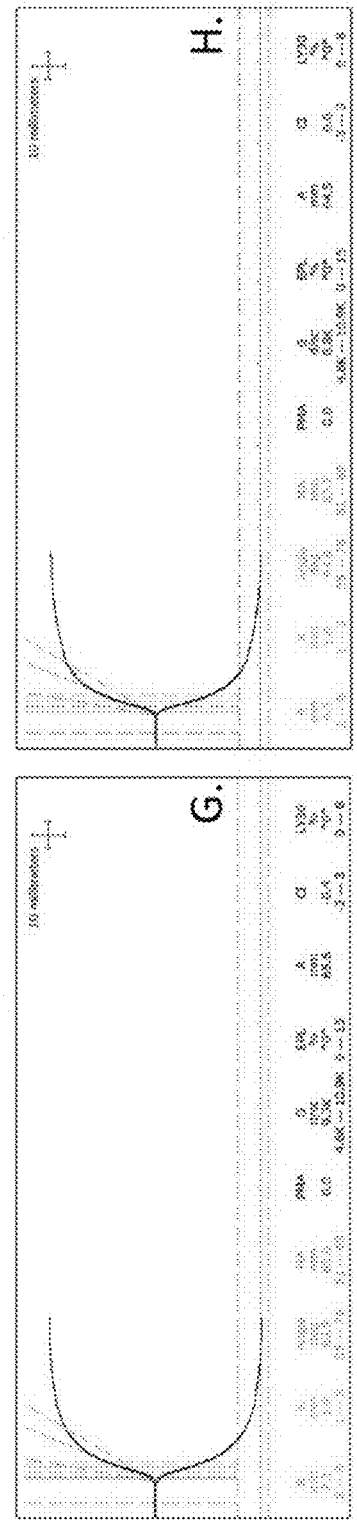
Fig. 14G
Fig. 14H

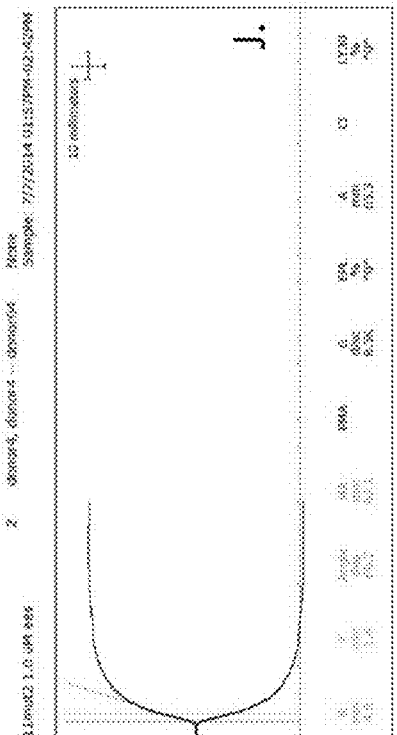
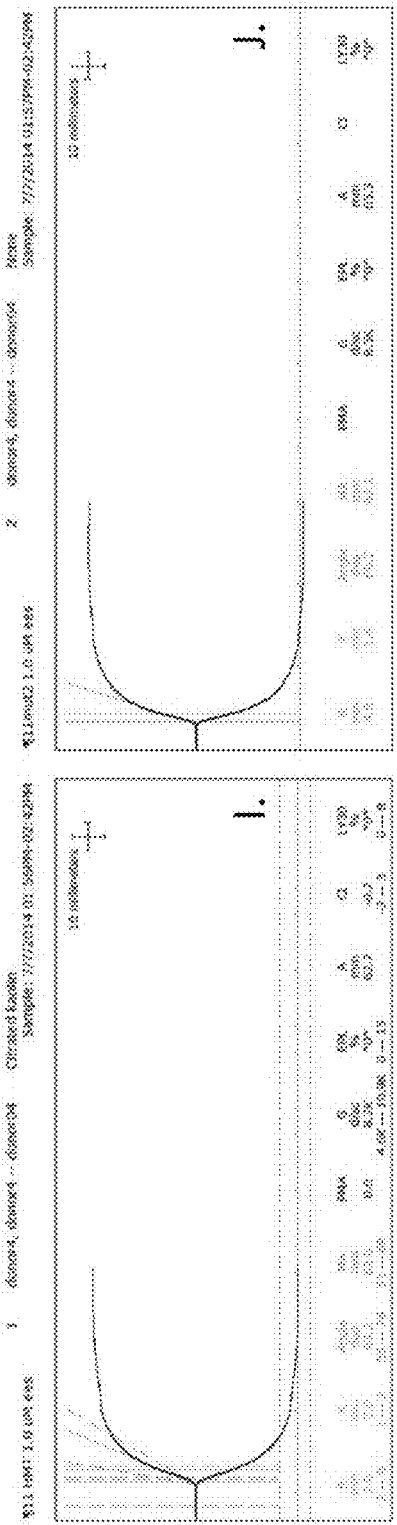
Figures 14I-J
Fig. 14I
Fig. 14J

SEQUENCE LISTING

```
<160> NUMBER OF SEQ ID NOS: 6

<210> SEQ ID NO 1
<211> LENGTH: 58
<212> TYPE: RNA
<213> ORGANISM: Artificial Sequence
<220> FEATURE:
<223> OTHER INFORMATION: Synthetic aptamer sequence: T18.3
<220> FEATURE:
<221> NAME/KEY: modified_base
<222> LOCATION: (1)..(58)
<223> OTHER INFORMATION: Each C and each U is 2F modified

<400> SEQUENCE: 1
ggacuuggau aaccucaccg caauggcggc uugucagacg acucgcugag gauccgag      58

<210> SEQ ID NO 2
<211> LENGTH: 49
<212> TYPE: RNA
<213> ORGANISM: Artificial Sequence
<220> FEATURE:
<223> OTHER INFORMATION: Synthetic aptamer sequence: 11 HMT
<220> FEATURE:
<221> NAME/KEY: modified_base
```

<222> LOCATION: (1)..(49)
<223> OTHER INFORMATION: Each C and each U is 2F modified

<400> SEQUENCE: 2
ggauccaacg cacaauuacg ugccuuguca gacgacucgc ugaggaucc          49

<210> SEQ ID NO 3
<211> LENGTH: 80
<212> TYPE: RNA
<213> ORGANISM: Artificial Sequence
<220> FEATURE:
<223> OTHER INFORMATION: Synthetic aptamer sequence: R8c7
<220> FEATURE:
<221> NAME/KEY: modified_base
<222> LOCATION: (1)..(80)
<223> OTHER INFORMATION: Each C and each U is 2F modified

<400> SEQUENCE: 3
gggaggacga ugcggucgcc caaacuugga uaaccucacc gcaauggcgg cuugucagac   60
gacucgcuga ggauccgaga                                              80

<210> SEQ ID NO 4
<211> LENGTH: 80
<212> TYPE: RNA
<213> ORGANISM: Artificial Sequence
<220> FEATURE:
<223> OTHER INFORMATION: Synthetic aptamer sequence: R9c11
<220> FEATURE:
<221> NAME/KEY: modified_base
<222> LOCATION: (1)..(80)
<223> OTHER INFORMATION: Each C and each U is 2F modified

<400> SEQUENCE: 4
gggaggacga ugcggucacg ccccucagga uccaacgcac aauuacgugc cuugucagac   60
gacucgcuga ggauccgaga                                              80

<210> SEQ ID NO 5
<211> LENGTH: 58
<212> TYPE: RNA
<213> ORGANISM: Artificial Sequence
<220> FEATURE:
<223> OTHER INFORMATION: Synthetic aptamer sequence: 18.3 Mut 1
<220> FEATURE:
<221> NAME/KEY: modified_base
<222> LOCATION: (1)..(58)
<223> OTHER INFORMATION: Each C and each U is 2F modified

<400> SEQUENCE: 5
ggacuuggau aaccucaccg caauggcgga gggucagacg acucgcugag gauccgag    58

<210> SEQ ID NO 6
<211> LENGTH: 49
<212> TYPE: RNA
<213> ORGANISM: Artificial Sequence
<220> FEATURE:
<223> OTHER INFORMATION: Synthetic aptamer sequence: 11 Mut 2
<220> FEATURE:
<221> NAME/KEY: modified_base
<222> LOCATION: (1)..(49)
<223> OTHER INFORMATION: Each C and each U is 2F modified

<400> SEQUENCE: 6
ggauccaacg cacaauuacg ugccgguuca gacgacucgc ugaggaucc          49

FACTOR V/VA-TARGETING APTAMER COMPOSITIONS AND METHODS OF USING THE SAME

CROSS-REFERENCE TO RELATED PATENT APPLICATIONS

The present application claims the benefit of priority to U.S. Provisional Patent Application No. 62/348,198, filed on Jun. 10, 2016, the content of which is incorporated herein by reference in its entirety.

STATEMENT REGARDING FEDERALLY SPONSORED RESEARCH

This invention was made with government support by the National Institutes of Health under Award Number RO1-HL065222. The government has certain rights in the invention.

INTRODUCTION

Anticoagulant agents are commonly used drugs to reduce blood coagulation in acute and chronic clinical settings. Many of these drugs target the common pathway of coagulation because it is critical for thrombin generation and disruption of this portion of the pathway has profound effects on the hemostatic process. Currently available drugs for these indications struggle with balancing desired activity with immunogenicity and poor reversibility or irreversibility in the event of hemorrhage. While improvements are being made with the current drugs, new drugs with better therapeutic indices are needed for surgical intervention and chronic indications to prevent thrombosis from occurring.

An essential component of the hemostatic process is the conversion of prothrombin to thrombin by the prothrombinase complex in the common pathway of coagulation. The prothrombinase complex is comprised of FXa, FVa, phospholipid surfaces, and calcium and rapidly activates prothrombin into α-thrombin to maintain hemostasis. FVa is a necessary cofactor for FXa in the prothrombinase complex to achieve maximal rates of α-thrombin generation, which is essential for bioamplification of the coagulation cascade and repair of vascular damage in the event of an injury. Reduced activity of this complex leads to impaired thrombin generation and an elevated risk of bleeding. However, in patient populations at risk for thrombotic events such as pulmonary embolism (PE), reducing the activity of this complex is an important aspect of managing their risk. Anticoagulants such as warfarin and direct thrombin or FXa inhibitors have been used to manage their increased thrombotic risk. While direct inhibitors of FXa are commercially available for use as anticoagulants, there have been no drugs developed to target FVa.

SUMMARY

In one aspect of the present invention, aptamers are provided. The aptamer may include a polynucleotide having at least 50%, 60%, 70%, 80%, 85%, 90%, 95%, or 99% sequence identity to SEQ ID NO: 1 or SEQ ID NO: 2. In some embodiments, the aptamer may include a polynucleotide having at least 50%, 60%, 70%, 80%, 85%, 90%, 95%, or 99% sequence identity to SEQ ID NO: 3 or SEQ ID NO: 4. In some embodiments, the aptamer may include SEQ ID NO: 1, SEQ ID NO: 2, SEQ ID NO: 3, or SEQ ID NO: 4.

In some embodiments, the aptamer may include a polynucleotide comprising from 5' to 3' the nucleotide sequence GGA, a first stem forming region consisting of 7 nucleotides, a first loop region consisting of the nucleotide sequence AA, a second stem forming region consisting of 4 nucleotides, a second loop region consisting of the nucleotide sequence A, a third stem forming region consisting of 4 nucleotides, a third loop region consisting of the nucleotide sequence AAUG, a fourth stem forming region consisting of 4 nucleotides and capable of forming a stem with the third stem forming region, a fourth loop region consisting of the nucleotide sequence CUU, a fifth stem forming region consisting of 3 nucleotides, a fifth loop region consisting of the nucleotide sequence AGAC, a sixth stem forming region consisting of 3 nucleotides and capable of forming a stem with the fifth stem forming region, a sixth loop region consisting of the nucleotide sequence UCGCU, a seventh stem forming region consisting of 4 nucleotides and capable of forming a stem with the second stem forming region, an eighth stem forming region consisting of 7 nucleotides and capable of forming a stem with the first stem forming region. A nonlimiting example of such an aptamer is SEQ ID NO: 1 (T18.3) as shown in FIG. 3.

In some embodiments, the aptamer may include a polynucleotide comprising from 5' to 3' a first stem forming region consisting of 6 nucleotides, a first loop region consisting of the nucleotide sequence AAC, a second stem forming region consisting of 4 nucleotides, a second loop region consisting of the nucleotide sequence AAUUAC, a third stem forming region consisting of 4 nucleotides and capable of forming a stem with the second stem forming region, a third loop region consisting of the nucleotide sequence CUUG, a fourth stem forming region consisting of 4 nucleotides, a fourth loop region consisting of the nucleotide sequence A, a fifth stem forming region consisting of 2 nucleotides, a fifth loop region consisting of the nucleotide sequence ACU, a sixth stem forming region consisting of 2 nucleotides and capable of forming a stem with the fifth stem forming region, a seventh stem forming region consisting of 4 nucleotides and capable of forming a stem with the fourth stem forming region, and an eighth stem forming region consisting of 6 nucleotides and capable of forming a stem with the first stem forming region. A nonlimiting example of such an aptamer is SEQ ID NO: 2 (11 HMT) as shown in FIG. 3.

In another aspect, antidotes are provided, the antidotes may include a polynucleotide having a nucleotide sequence reverse complementary to and capable of hybridizing to at least 8, 9, 10, 11, 12 or more nucleotides of any one of the aptamers described herein.

In a further aspect, the present invention relates to pharmaceutical compositions including any of the aptamers or antidotes described herein.

In a still further aspect, the present invention relates to methods for preventing blood clot formation in a subject. The methods may include administering to the subject any one of the aptamer compositions described herein in a therapeutically effective amount to prevent blood clot formation in the subject.

BRIEF DESCRIPTION OF THE DRAWINGS

FIG. 10 shows competition of T18.3 and 11HMT for Binding to FV. FIG. 10A shows Cold 11HMT competition with hot T18.3. FIG. 10B shows Cold T18.3 competition with hot 11 HMT.

FIG. 11A shows T18.3 versus 18.3Mut1 titration curve. FIG. 11B shows T18.3 fold increase in clot time over mutant. FIG. 11C shows 11HMT versus 11Mut2 titration curve. FIG. 11D shows 11HMT fold increase over mutant.

FIG. 12 shows Prothrombin Time Titration of T18.3 and 11HMT. FIG. 12A shows T18.3 versus 18.3Mut1 dose titration. FIG. 12B shows T18.3 fold increase in clot time over mutant. FIG. 12C shows 11HMT versus 11Mut2 dose titration. FIG. 12D shows 11HMT fold increase in clot time over mutant.

FIG. 14 shows Whole Blood Thromboelastography with T18.3 and 11HMT. FIGS. 14A and 14B show buffer control. FIG. 14 C shows T18.3 at 300 nM. FIG. 14D shows 18.3Mut1 at 300 nM. FIG. 14E shows T18.3 at 1.0 μM. FIG. 14F shows 18.3Mut1 at 1.0 μM. FIG. 14G shows 11HMT at 300 nM. FIG. 14H shows 11Mut2 at 300 nM. FIG. 14I shows 11HMT at 1.0 μM. FIG. 14J shows 11Mut2 at 1.0 μM.

FIG. 15 shows PPP and PRP TEG Tracings with 1.0 μM T18.3.

FIG. 18 shows Cross Reactivity of T18.3 and 11HMT with Animal Plasmas.

DETAILED DESCRIPTION

Figure 1:
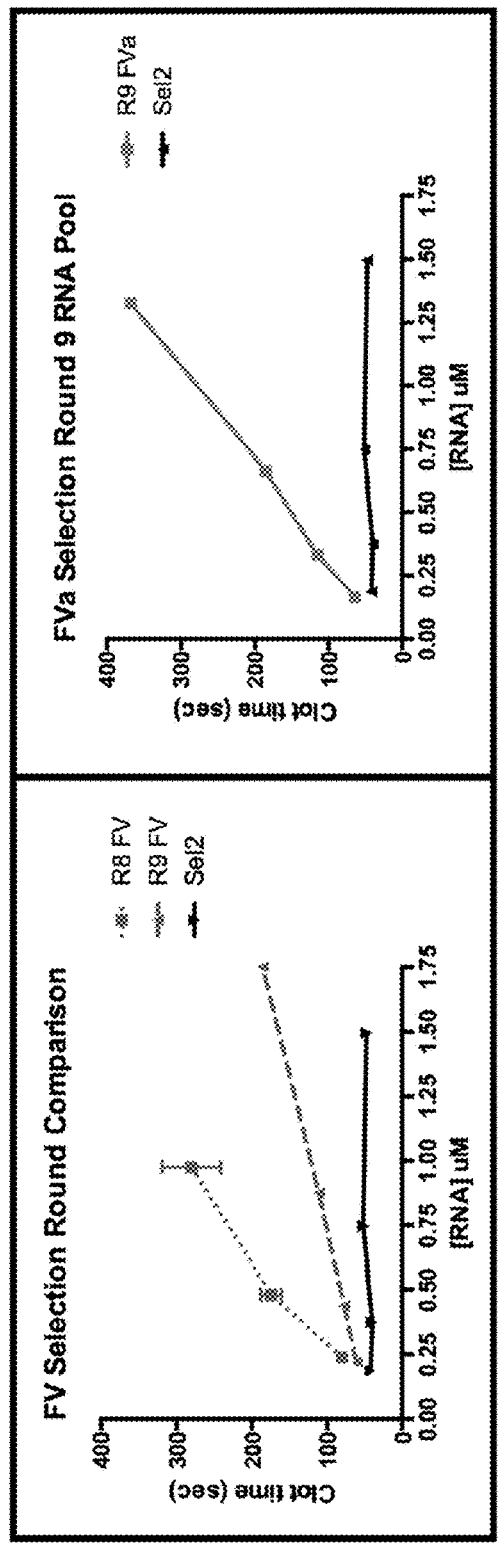
FIG. 1 shows graphs of aPTT assays of RNA aptamer selection from the indicated rounds of selection from FV (left) and FVa (right) selections.

Here, in the non-limiting Examples, the present inventors generated aptamers able to inhibit the procoagulant activity of Factor V ("FV") and/or Factor Va ("FVa") using the combinatorial chemistry technique of SELEX. The biochemical and anticoagulant properties of the developed aptamers were analyzed and a unique method of anticoagulant activity was discovered. Without being limited by theory, the present inventors hypothesize that because FV circulates at a low concentration and hemostasis can be maintained near normal with very little functional FV, this protein may be a potentially useful anticoagulant target. As a cofactor, FVa lacks an active site and has not been the target of small molecule development as a result. Thus, aptamers, polynucleotide therapeutics that do not require active sites to exert inhibitory activity, may be a good way of generating an anticoagulant directed at a cofactor. Additionally, because only a small amount is needed for normal hemostasis, FVa may represent a safer target for anticoagulant development.

Disclosed herein are compositions of aptamers and antidotes as well as methods for preventing blood clots in a subject using the newly discovered Factor V/Factor Va-targeting aptamers. These compositions and methods may be useful in several applications including, without limitation, prevention of thrombi (in vitro, in vivo, or ex vivo), or the prevention or treatment of thrombi associated with stroke, cerebrovascular thrombi, deep vein thrombosis (DVT), pulmonary embolism (PE), atrial fibrillation, coronary artery thrombus, intra-cardiac thrombi, post-surgical thrombi, cancer-induced thrombosis, cancer-related thrombin expression, infection, and disseminated intravascular coagulation (DIC).

Aptamers are provided herein. As used herein, the term "aptamer" refers to single-stranded oligonucleotides that bind specifically to target molecules with high affinity. Aptamers can be generated against target molecules, such as FV and FVa, by screening combinatorial oligonucleotide libraries for high affinity binding to the target (See, e.g., Ellington and Szostak, Nature 1990; 346: 8 18-22 (1990), Tuerk and Gold, Science 249:505-10 (1990)). The aptamers disclosed herein may be synthesized using methods well-known in the art. For example, the disclosed aptamers may be synthesized using standard oligonucleotide synthesis technology employed by various commercial vendors including Integrated DNA Technologies, Inc, (IDT), Sigma-Aldrich, Life Technologies, or Bio-Synthesis, Inc.

The aptamer may include a polynucleotide having at least 50%, 60%, 70%, 80%, 85%, 90%, 95%, or 99% sequence identity to SEQ ID NO: 1 or SEQ ID NO: 2. In some embodiments, the aptamer may include a polynucleotide having at least 50%, 60%, 70%, 80%, 85%, 90%, 95%, or 99% sequence identity to SEQ ID NO: 3 or SEQ ID NO: 4.

In some embodiments, the aptamer may include SEQ ID NO: 1, SEQ ID NO: 2, SEQ ID NO: 3, or SEQ ID NO: 4.

The terms "polynucleotide," "nucleotide sequence," "polynucleotide sequence," "nucleic acid" and "nucleic acid sequence" refer to a nucleotide, oligonucleotide, polynucleotide (which terms may be used interchangeably), or any fragment thereof. These phrases may refer to DNA or RNA of genomic, natural, or synthetic origin.

Regarding nucleotide sequences, the terms "sequence identity," "percent identity," and "% identity" refer to the percentage of base matches between at least two nucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Sequence identity for a nucleotide sequence may be determined as understood in the art. A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastn," that is used to align a known nucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website.

Regarding nucleotide sequences, sequence identity is measured over the length of an entire defined nucleotide sequence, for example, as defined by a particular sequence identified herein. Furthermore, sequence identity, as measured herein, is based on the identity of the nucleotide base in the nucleotide sequence, irrespective of any further modifications to the nucleotide sequence. For example, the nucleotide sequences in the tables described herein may include modifications to the nucleotide sequences such 2'flouro, 2'O-methyl, and inverted deoxythymidine (idT) modifications. These modifications are not considered in determining sequence identity. Thus if a base, for example, is a 2'fluoro adenine (or 2'O-methyl, etc.), it is understood to be an adenine for purposes of determining sequence identity with another sequence.

Figure 3:
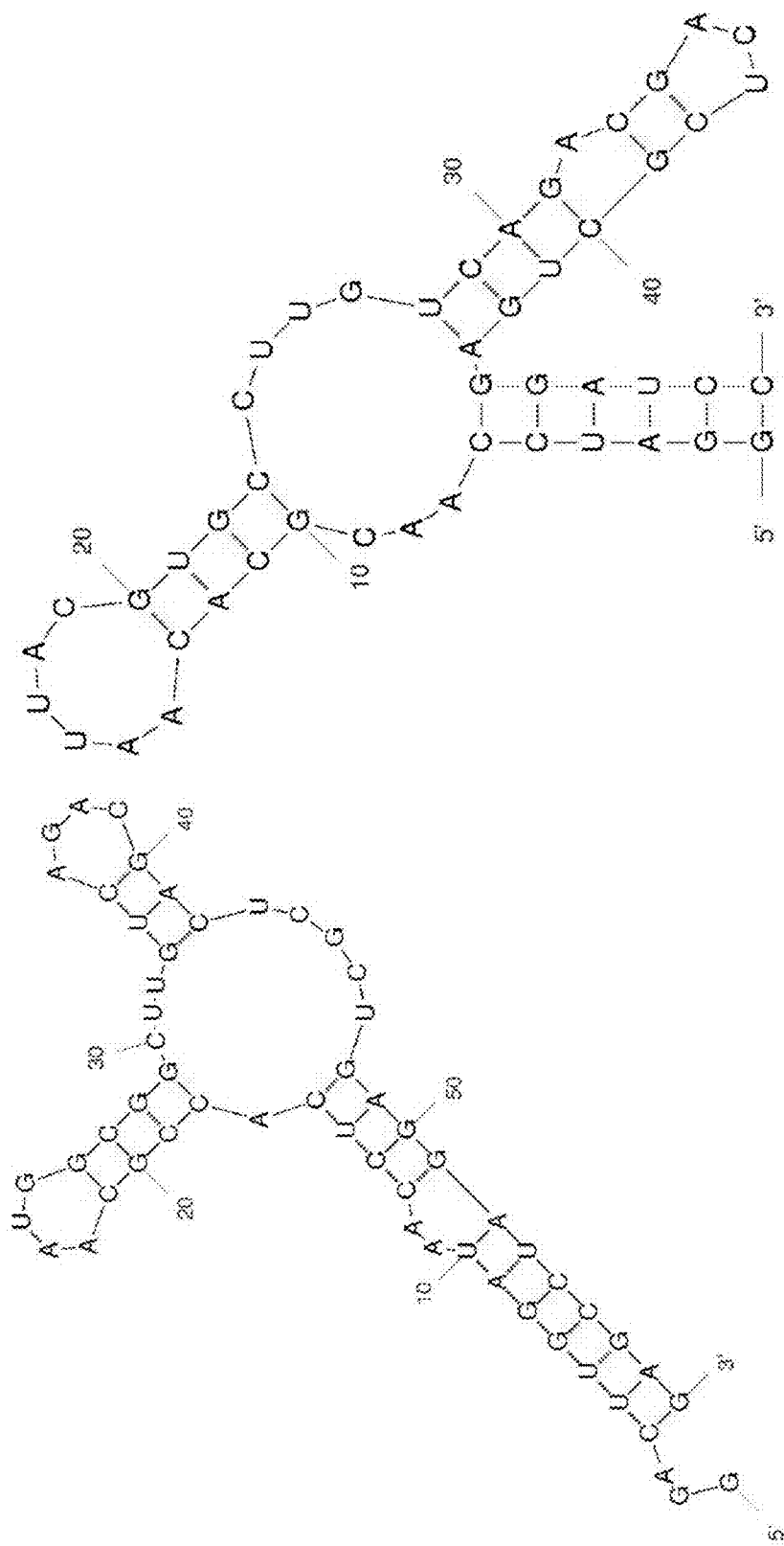
FIG. 3 shows truncated lead aptamers. Left: T18.3 (SEQ ID NO: 1). Right: 11HMT (SEQ ID NO: 2).

In some embodiments, the aptamer may include a polynucleotide comprising from 5' to 3' the nucleotide sequence GGA, a first stem forming region consisting of 7 nucleotides, a first loop region consisting of the nucleotide sequence AA, a second stem forming region consisting of 4 nucleotides, a second loop region consisting of the nucleotide sequence A, a third stem forming region consisting of 4 nucleotides, a third loop region consisting of the nucleotide sequence AAUG, a fourth stem forming region consisting of 4 nucleotides and capable of forming a stem with the third stem forming region, a fourth loop region consisting of the nucleotide sequence CUU, a fifth stem forming region consisting of 3 nucleotides, a fifth loop region consisting of the nucleotide sequence AGAC, a sixth stem forming region consisting of 3 nucleotides and capable of forming a stem with the fifth stem forming region, a sixth loop region consisting of the nucleotide sequence UCGCU, a seventh stem forming region consisting of 4 nucleotides and capable of forming a stem with the second stem forming region, an eighth stem forming region consisting of 7 nucleotides and capable of forming a stem with the first stem forming region. A nonlimiting example of such an aptamer is SEQ ID NO: 1 (T18.3) as shown in FIG. 3.

In some embodiments, the aptamer may include a polynucleotide comprising from 5' to 3' a first stem forming region consisting of 6 nucleotides, a first loop region consisting of the nucleotide sequence AAC, a second stem forming region consisting of 4 nucleotides, a second loop region consisting of the nucleotide sequence AAUUAC, a third stem forming region consisting of 4 nucleotides and capable of forming a stem with the second stem forming region, a third loop region consisting of the nucleotide sequence CUUG, a fourth stem forming region consisting of 4 nucleotides, a fourth loop region consisting of the nucleotide sequence A, a fifth stem forming region consisting of 2 nucleotides, a fifth loop region consisting of the nucleotide sequence ACU, a sixth stem forming region consisting of 2 nucleotides and capable of forming a stem with the fifth stem forming region, a seventh stem forming region consisting of 4 nucleotides and capable of forming a stem with the fourth stem forming region, and an eighth stem forming region consisting of 6 nucleotides and capable of forming a stem with the first stem forming region. A nonlimiting example of such an aptamer is SEQ ID NO: 2 (11 HMT) as shown in FIG. 3.

In some embodiments, the aptamer may bind to Factor V or Factor Va with a dissociation constant ($K_D$) of no more than 500 nM, 100 nM, 50 nM, 25 nM, 10 nM, 1 nM, 0.1 nM, or 0.01 nM. Methods for determining the binding affinity of an aptamer are known by those of ordinary skill in the art and may include, as used in the. Examples, using a Biacore™ SPR system.

The aptamers may include a polynucleotide (RNA, DNA, LNA (locked nucleic acid) or peptide nucleic acid (PNA)) that is in an unmodified form or may be in a modified form including at least one nucleotide base modification. Nucleotide base modifications of polynucleotides to, for example, protect the polynucleotide from nuclease degradation and/or increase the stability of the polynucleotide are well-known in the art. Common nucleotide base modifications that may be used in accordance with the present invention include, without limitation, deoxyribonucleotides, 2'-O-Methyl bases, 2'-Fluoro bases, 2' Amino bases, inverted deoxythymidine bases, 5' modifications, and 3' modifications. In some embodiments, the aptamer may include a polynucleotide including at least one nucleotide base modification selected from the group consisting of a 2'fluoro modification, a 2'O-methyl modification, a 5' modification, and a 3' modification.

As exemplary 5' and/or 3' modifications, the aptamer may include a polynucleotide including a 5' linker and/or a 3' linker. Common 5' and/or 3' linkers for polynucleotides are known in the art and may include peptides, amino acids, nucleic acids, as well as homofunctional linkers or heterofunctional linkers. Particularly useful conjugation reagents that can facilitate formation of a covalent bond with an aptamer may comprise an N-hydroxysuccinimide (NHS) ester and/or a maleimide or using click chemistry. Typical 5' and/or 3' linkers for polynucleotides may include without limitation, amino C3, C4, C5, C6, or C12-linkers.

The aptamer may further include a stability agent. As used herein, a "stability agent" refers to any substance(s) that may increase the stability and/or increase the circulation time of a polynucleotide in vivo. Typical stability agents are known in the art and may include, without limitation, polyethylene glycol (PEG), cholesterol, albumin, or Elastin-like polypeptide.

The aptamer and stability agent may be "linked" either covalently or non-covalently. Additionally, the aptamer and stability agent may be linked using the 5' and/or 3' linkers described herein. The aptamer and stability agent may be linked at the 5' end and/or the 3' end of the aptamer. To link the aptamer and stability agent non-covalently, the aptamer and the stability agent may be linked by a tag system. A "tag system" may include any group of agents capable of binding one another with a high affinity. Several tag systems are well-known in the art and include, without limitation, biotin/avidin, biotin/streptavidin, biotin/NeutrAvidin, or digoxigenin (DIG) systems. In some embodiments, the tag system comprises biotin/avidin or biotin/streptavidin. In such embodiments, the aptamer may be modified at either the 5' or 3' end to include biotin while the stability agent may be modified to include streptavidin or avidin. Alternatively, the aptamer may be modified at either the 5' or 3' end to include streptavidin or avidin while the stability agent may be modified to include biotin.

Dimers, trimers, and tetramers including any one of the aptamers described herein are also provided. A "dimer" refers to the linking together of two aptamer molecules in order to, for example, to increase the stability and/or increase the circulation time of a polynucleotide in vivo. A "trimer" refers to the linking together of three aptamer molecules in order to, for example, to increase the stability and/or increase the circulation time of a polynucleotide in vivo. A "tetramer" refers to the linking together of four aptamer molecules in order to, for example, to increase the stability and/or increase the circulation time of a polynucleotide in vivo. The aptamer molecules may be linked together covalently, non-covalently, or a combination of both. The aptamer molecules may be linked at their 5' or 3' ends. To link the aptamers non-covalently, the aptamers may be linked by a tag system or through a scaffold system.

Antidotes are also provided herein, the antidote may include a polynucleotide having a nucleotide sequence reverse complementary to and capable of hybridizing to at least 8, 9, 10, 11, 12 or more nucleotides of any one of the aptamers described herein. The antidotes are capable of blocking or reversing the activity of the aptamer.

Pharmaceutical compositions including any of the aptamers or antidotes described herein are provided. The pharmaceutical compositions may include a pharmaceutical carrier, excipient, or diluent (i.e., agents), which are nontoxic to the cell or mammal being exposed thereto at the dosages and concentrations employed. Often a pharmaceutical agent is in an aqueous pH buffered solution. Examples of pharmaceutical carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ brand surfactant, polyethylene glycol (PEG), and PLURONICS™ surfactant.

Methods for preventing blood clot formation in a subject are provided. The methods may include administering to the subject any one of the aptamer compositions described herein in a therapeutically effective amount to prevent blood clot formation in the subject. "Preventing blood clot formation" may include reducing the likelihood of blood clots, reducing the size of blood clots or slowing further progression of blood clotting.

As used herein, the term "subject" refers to both human and non-human animals. The term "non-human animals" of the disclosure includes all vertebrates, e.g., mammals and non-mammals, such as non-human primates, sheep, dog, cat, horse, cow, mice, chickens, amphibians, reptiles, and the like. In some embodiments, the subject is a human patient.

The subject in need of blood clot prevention may need prevention of blood clots associated with, for example without limitation, stroke, cerebrovascular thrombi, deep vein thrombosis (DVT), pulmonary embolism (PE), atrial fibrillation, coronary artery thrombus, intra-cardiac thrombi, post-surgical thrombi, cancer-induced thrombosis, cancer-related thrombin expression, infection, disseminated intravascular coagulation (DIC), and arterial thrombosis including cerebral arteries, coronary arteries and peripheral arteries in the head and neck, visceral arteries, arm arteries and leg arteries. In some embodiments, the subject in need of blood clot prevention may suffer from FV Leiden, atrial fibrillation, or be at risk of having a Deep Vein Thrombosis, a stroke, a heart attack, or a pulmonary embolism.

The aptamer and antidote compositions disclosed herein may be of particular use in subjects with homozygous or heterozygous FV Leiden mutations who would benefit from safe, low-level anticoagulation. Management of patients with FV Leiden includes chronic anticoagulation, however none of the currently used anticoagulants actually target the protein that is mutated because no drugs exist that inhibit FV/FVa. Without being limited by theory, the inventors postulate that an anticoagulant that is able to reduce the overall number of FVa molecules that can create a functional complex could reduce their risk of thrombotic morbidities. The disclosed aptamer and antidote compositions may also be useful in acute anticoagulation with patients who have any form of thrombophilia that need additional anticoagulation to reduce the risk of thrombosis.

A therapeutically effective amount or an effective amount as used herein means the amount of a composition that, when administered to a subject for preventing or treating a blood clot is sufficient to effect a treatment (as defined above). The therapeutically effective amount will vary depending on the formulation or composition, the disease and its severity and the age, weight, physical condition and responsiveness of the subject to be treated.

The methods of preventing or treating blood clots described herein may further include administering to the subject an antidote in a therapeutically effective amount to neutralize the aptamer. "Neutralizing" the aptamer refers to decreasing either the anti-thrombotic or thrombolytic activity of the aptamer.

Antidotes that may be used in accordance with the present methods may include sequence-specific antidotes such as the antidotes described herein. The antidotes may also include sequence non-specific antidotes (i.e., cationic polymers) described in, for example, WO/2008/121354.

The compositions (i.e. aptamers, antidotes, and pharmaceutical compositions) described herein may be administered by any means known to those skilled in the art, including, but not limited to, oral, topical, intranasal, intraperitoneal, parenteral, intravenous, intramuscular, subcutaneous, intrathecal, transcutaneous, nasopharyngeal, intralesional, intra-tumoral, intradermal, or transmucosal absorption. Thus the compositions may be formulated as an ingestable, injectable, topical or suppository formulation.

Administration of the compositions to a subject in accordance with the invention may exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the composition or compositions being administered, the disease to be treated or inhibited, the condition of the subject, and other relevant medical factors that may modify the activity of the compositions or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions described herein and of a known agent, such as by means of an appropriate conventional pharmacological protocol.

The maximal dosage for a subject is the highest dosage that does not cause undesirable or intolerable side effects. The number of variables in regard to an individual treatment regimen is large, and a considerable range of doses is expected. The route of administration will also impact the dosage requirements. It is anticipated that dosages of the compositions will prevent or treat or reduce blot clots by at least 10%, 20%, 30%, 40%, 50%, 60%, 70%, 80%, 90%, 100% or more as compared to no treatment.

The compositions described herein may be administered one time or more than one time to the subject to effectively prevent blood clots. Suitable dosage ranges are of the order of several hundred micrograms effective ingredient with a range from about 0.01 to 10 mg/kg/day, preferably in the range from about 0.1 to 1 mg/kg/day. Precise amounts of effective ingredient required to be administered depend on the judgment of the practitioner and may be peculiar to each subject. It will be apparent to those of skill in the art that the therapeutically effective amount of the compositions described herein will depend, inter alia, upon the administration schedule, the unit dose of drug administered, whether the composition is administered in combination with other therapeutic agents, the status and health of the recipient, and the therapeutic activity of the particular composition.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Example 1—Development and Characterization of an RNA Aptamers Targeting Coagulation CoFactor FV and FVa Materials and Methods
Aptamer Generation Soluble SELEX was used to generate aptamers to modified FV and FVa in parallel. The modifications to FV and FVa have been described previously and validated to behave like plasma-derived FV and FVa. Modified forms of the proteins were utilized because FV and FVa are highly sensitive to proteolysis for activation and inactivation of the cofactor activity. Generation of a functional aptamer from the SELEX process is dependent upon the quality of the target protein.

The architecture of the starting library, Sel2, included fixed regions on the 5' and 3' ends flanking a 40 nucleotide randomized region. The randomized region was generated with equal molar amounts of each base, which allows for diversity of up to 440 sequences. The starting round contained approximately 1014 sequences based on the amount of input RNA for the first round of selection. While this did not cover all possible sequences, this amount of diversity was sufficient to allow for identification of anticoagulant aptamers targeting FV and FVa.

Additional modification to the starting library included 2'F-modified pyrimadines (2'-fluorouracil and 2'-fluorocytosine) for increased stability in the presence of plasma proteases. Nine rounds of selection with increasing stringency were performed and rounds eight and nine were assayed for anticoagulant activity using an activated partial thromboplastin time (aPTT) clotting assay. To identify aptamer sequences, round eight and nine PCR products were digested with EcoR1 and BamH1, inserted into a pUC19 vector, mini-prepped, and sent for DNA sequencing at Eton Biosciences (Research Triangle Park, NC). Individual sequences were tested for anticoagulant activity in an aPTT and binding affinity of sequences with anticoagulant activity was approximated using a nitrocellulose-based binding assay (see assays descriptions below). A lead aptamer was identified for each selection (FV, R8c7 and FVa, R9c11) based on anticoagulant activity and binding affinity relative to other functional sequences (Table 1).

Truncation of FV R8c7 was attempted by reducing stem length in the parent aptamers, with particular emphasis placed on eliminated AU base pairs. Additionally, antidotes to 18 nucleotide stretches of the parent aptamer R8c7 were used to identify sequences dispensable for activity, which generated a truncate that was 60 nucleotides long and named T18 (sequence not shown). From this shorter truncate, a panel of truncates were created and the truncation strategy was switched back to the elimination of AU base pairs. The T18.3 aptamer was designated as the final truncated aptamer generated from R8c7 and was 58 nucleotides in length and used for all further characterization studies (Table 1).

Generation of Mutant Aptamers

Two or three mutant aptamers were created by transversion of three nucleotides in the predicted loops of each aptamer (Table 1). The mutants for each aptamer were assayed for anticoagulant function and ability to bind the target protein using nitrocellulose-based binding assays. Mutants were selected if they showed zero anticoagulant activity and no ability to bind the target protein above that observed by the starting library. The mutant aptamer for T18.3 was designated 18.3Mut1 and the mutant aptamer for 11HMT was designated 11Mut2 (Table 1).

Dephosphorylation & 5'-End Radiolabeling

Bacterial alkaline phosphatase (Life Technologies, Carlsbad, Calif.) was used to dephosphorylate the in vitro transcribed RNAs. Individual or pooled (SELEX round) RNAs were incubated at 65° C. for 1 hour followed by phenol/chloroform/isoamyl alcohol extraction and ethanol precipitation. T4 polynucleotide kinase (New England Biolabs, Ipswich, Mass.) was used to add a 5'-[γ32P] ATP (Perkin Elmer, Waltham, Mass.) to radiolabel the dephosphorylated

TABLE 1

Full length and truncated aptamer sequences where C's and U's are 2'F modified.

| Aptamer Name | Sequence 5'-3' | Length in nts |
|---|---|---|
| T18.3 | GGACUUGGAUAACCUCACCGCAAUGGCGGCUUGUCAGACGA CUCGCUGAGGAUCCGAG (SEQ ID NO: 1) | 58 |
| 11 HMT | GGAUCCAACGCACAAUUACGUGCCUUGUCAGACGACUCGCU GAGGAUCC (SEQ ID NO: 2) | 49 |
| R8c7 | GGGAGGACGAUGCGGUCGCCCAAACUUGGAUAACCUCACCG CAAUGGCGGCUUGUCAGACGACUCGCUGAGGAUCCGAGA (SEQ ID NO: 3) | 80 |
| R9c11 | GGGAGGACGAUGCGGUCACGCCCCUCAGGAUCCAACGCAC AAUUACGUGCCUUGUCAGACGACUCGCUGAGGAUCCGAGA (SEQ ID NO: 4) | 80 |
| 18.3 Mut 1 | GGACUUGGAUAACCUCACCGCAAUGGCGGAGGGUCAGACGA CUCGCUGAGGAUCCGAG (SEQ ID NO: 5) | 58 |
| 11 Mut 2 | GGAUCCAACGCACAAUUACGUGCCGGUUCAGACGACUCGCU GAGGAUCC (SEQ ID NO: 6) | 49 |

Aptamer Truncation

Each lead aptamer was systematically truncated to a shorter, functional length. The FVa R9c11 aptamer was reduced to 49 nucleotides directly from the full length of 80 nucleotides. The truncated aptamer was renamed 11HMT to reflect a difference in sequence from the parent aptamer (Table 1). This truncated aptamer was used for further characterization studies.

RNAs. Counts per million (CPM) readings for individual and pooled radiolabeled RNAs were obtained using the Tri-Carb 2800TR Liquid Scintillation Analyzer (Perkin Elmer, Waltham, Mass.). An online calculator from GraphPad Prism was used to calculate percent decay of radiolabeled samples when labeled RNAs were used more than 1-2 days after the initial labeling reaction to ensure the correct number of counts was used in each binding experiment.

Double Filter Nitrocellulose Binding Assay

Apparent binding affinity of the aptamers to a purified protein was determined using double filter nitrocellulose binding assays. Binding of the radiolabeled pooled RNA, 11HMT, and 11Mut2 to modified FV and FVa was assessed by incubating trace amounts of radiolabeled RNA with serial dilutions of the purified target protein. For SELEX round binding, pooled RNAs were incubated with modified FV or FVa diluted two fold from 0 nM to 750-800 nM for both proteins. For 11HMT, the radiolabeled RNAs were incubated with both proteins from 0 nM to 500 nM. The radiolabeled RNAs were denatured and re-folded in Hepes-buffered saline (HBS) with CaCl2 (20 mM Hepes pH 7.4, 150 mM NaCl, 2 mM CaCl2), 0.01% bovine serum albumin (BSA), and 0.1% w/v polyethylene glycol 8000 (PEG 8000) by incubating at 95° C. for 3 minutes followed by cooling to room temperature for 3 minutes. The radiolabeled RNA alone was incubated at 37° C. for 5 minutes, followed by incubation with the protein in HBS with CaCl2, 0.01% BSA, and 0.1% w/v PEG 8000 at 37° C. for 5 minutes. The RNA-protein complexes were partitioned from unbound RNA with a 0.45 μm nitrocellulose (VWR, Radnor, Pa.) and nylon (Perkin-Elmer, Waltham, Mass.) membrane sandwich followed by a 100 μL wash with HBS with CaCl2 without BSA or PEG 8000. Bound and unbound RNA was quantitated using a Storm 825 phosphoimager (GE Healthcare, Little Chalfont, Buckinghamshire, UK) and quantified via densitometry. The corrected fraction bound was determined for each protein concentration and a non-linear regression one site binding fit was applied in GraphPad Prism 6 to determine the apparent KD.

Surface Plasmon Resonance (SPR)

The T18.3 binding constants were determined using surface plasmon resonance (SPR) with a BiaCore3000 (GE Healthcare). This method was used to determine apparent KDs for T18.3 to modified FV, modified FVa, the FV heavy chain, and the FV light chain. The T18.3 aptamer was synthesized (Biosynthesis, Lewisville, Tex.) and included a biotin and PEG 11 spacer on the 5' end to allow for immobilization of the aptamer on a biotin CAPture chip kit (GE Healthcare). Prior to chip coating, the biotinylated T18.3 was refolded using the same protocol as the in vitro transcribed T18.3 by heating to 95° C. for 3 minutes followed by 3 minutes at room temperature. Aptamer conjugation onto the chip was achieved by flowing aptamer solution over the chip at a rate of 2 μL/min for 5 minutes. For binding to the modified FV, FVa, and purified FV heavy chain, 5.0 ng of aptamer was coated onto the chip. For the purified FV light chain experiments 15.3 ng of aptamer was coated onto the chip. Binding experiments using SPR was performed at 25° C. in HBS with CaCl2, without the addition of BSA or PEG 8000. The proteins were diluted immediately prior to running the experiment and remained at room temperature until autoinjected into the microfluidics chamber for binding using the Inject or BigInject command in the BiaCore software. Table 2 details protein ranges assayed, flow rates, and contact times. Increasing concentrations of protein were flowed over the T18.3-coated chip and apparent KD was determined by calculating the differences in response units (RU) from buffer for each protein concentration immediately before the end of each protein injection and plotted as ΔRU versus protein concentration. The resulting points were fitted to a rectangular hyperbola to calculate the apparent KD. Each protein was tested in triplicate and the apparent KD for each run was reported.

TABLE 2

BIAcore 3000 Binding Parameters for Biotinylated T18.3

| Protein | Range Assayed (nM) | Flow Rate (μL/min) | Injection (min) |
|---|---|---|---|
| FVa | 0-60 | 8-12 | 15-25 |
| FV | 0-200 | 8-12 | 15-25 |
| Heavy Chain | 0-400 | 20 | 25 |
| Light Chain | 0-300 | 8 | 20-37 |

Coagulometer Assays

The effects of the aptamers on an activated partial thromboplastin time (aPTT) and prothrombin time (PT) assays were determined using a STart4 coagulometer (Diagnostica Stago, Asnieres sur Seine Cedex, France). Aptamers were denatured and re-folded in HBS with CaCl2 by incubation at 95° C. for 3 minutes then cooling to room temperature for 3 minutes. For the aPTT, 50 μL of pooled normal human platelet poor plasma (PPP) (George King Biomedical, Overland Parks, Kans.) was incubated with 5 μL of aptamer(s) for 5 minutes at 37° C., then 50 μL of aPTT-XL reagent (Pacific Hemostatics) was added and incubated for another 5 minutes at 37° C. Clotting was initiated by 50 μL of 0.025 M CaCl2 and the time to clot formation was recorded. For the PT, 50 μL of pooled normal human PPP was incubated with 5 μL of aptamer for 5 minutes at 37° C. before 100 μL of TriniClot PT Excel reagent was added to initiate clotting. When reversal of 11HMT and T18.3 was assayed in an aPTT, a third 5-minute incubation with 5 μL of protamine sulfate was performed prior to initiation of clotting with CaCl2. The protamine sulfate was serially diluted in HBS with CaCl2 and added in 5 μL to the assay to achieve the designated μg amount indicated on the X axis.

Species cross reactivity for T18.3 and 11HMT was determined using an aPTT assay. Pooled, mixed gender, platelet-poor animal plasmas (Biochemed) were incubated with 2.5 μM (final concentration) of functional and mutant aptamer for 5 min at 37° C., followed by addition of 50 μL of aPTT-XL reagent and incubated for an additional 5 min at 37° C. The addition of 50 μL of 0.025 M CaCl2 initiated clotting. Clot times for the functional and mutant aptamers were plotted with the baseline clot times for each species. Species tested for aptamer cross reactivity included common laboratory model species, as well as non-human primates.

Thromboelastography

Freshly drawn human blood from healthy volunteers was obtained following an approved IRB protocol. Blood was collected into 3.2% sodium citrate tubes and kept at room temperature for use in whole blood thromboelastography (TEG) assays with a TEG 5000 (Haemonetics, Braintree, Mass.). Aptamers were diluted in HBS with CaCl2 and denatured and refolded at 95° C. for three minutes followed by cooling to room temperature for three minutes. Clotting was stimulated in TEG assays using 10 μL of citrated kaolin (Haemonetics, Braintree, Mass.) from the 40 μL aliquots available from Haemonetics. Because the kaolin was a suspension, not in solution, when more than four assays were being run, 40 μL kaolin aliquots were combined and vortexed to ensure even distribution of activator within the suspension and to reduce variability between experiments. Prior to the addition of the blood solution, 20 μL of CaCl2 was added to the TEG cup to ensure thorough mixing upon addition of the blood. Addition of 340 μL blood solution, containing 320 μL of blood with 10 μL of aptamer and 10 μL of citrated kaolin, to the 20 μL of CaCl2 brought the assay to the correct volume and final concentrations. Prior to running any experimental assays, normal blood clot formation was validated by following a tracing of blood with of HBS with CaCl2 for 20-30 minutes, with particular emphasis placed on the lag time being in the normal range of 2-8 minutes. Experimental assay tracings were followed for 15 to 180 minutes after validation of normal blood clot tracing in the presence of HBS with CaCl2. Parameters of interest include R, lag time before clot formation, a, the angle indicating the rate of clot formation, and MA, the maximum amplitude, which is a surrogate for clot strength.

Thromboelastography was also performed on platelet-rich and platelet-poor plasma samples with slight modification. When running platelet-rich samples, the number of platelets/µL must be normalized to 150,000 platelets/µL by dilution with PPP generated from the same individual. The 20 µL of CaCl2 was added to the cup prior to the addition of 340 µL of a solution containing 20 µL kaolin, 10 µL aptamer, and 310 µL of PRP or PPP, making the reaction volume the same as with whole blood. The parameters of interest remain the same, however, the MA parameter is greatly reduced in PPP due to the lack of platelets.

Prothrombin Cleavage

Reaction mixtures of 200 µL containing FVa, T18.3, 18.3Mut1, 11HMT, or 11Mut2 at varying concentrations, 75:25 phosphatidylcholine and phosphatidylserine (PCPS) extruded vesicles, a prothrombin-like substrate, and FXa were incubated at 25° C. For reactions with Q271 prothrombin, the aptamers were pre-incubated with FVa and reaction buffer (20 mM Hepes, 150 mM NaCl, 0.1% w/v PEG 8000, 0.03% Tween 20, pH 7.5) for 4 minutes at 25° C. in a circulating water bath. Reactions were removed from the bath and PCPS vesicles and FXa were added and vortexed together. The t=0 timepoint was removed diluted into quench buffer (20 mM Hepes, 150 mM NaCl, 50 mM EDTA, pH 7.5) in a 96 well flat-bottom plate. The reaction mixture was initiated with the addition of the Q271 prothrombin. For reactions with desGlaQ271 prothrombin, the same pre-incubation scheme of aptamer with FVa was followed. After incubation, PCPS vesicles and desGlaQ271 was added to the reaction mixture, vortexed, and the t=0 timepoint removed to quench buffer. The reaction was initiated by the addition FXa. At 30, 60, 90, 120, and 180 seconds aliquots of the reaction mixture was removed and mixed into quench buffer stop further cleavage of prothrombin. Quenched reactions were further diluted in quench buffer and immediately prior to scanning at 405 nm in a Gemini kinetic plate reader (Molecular Devices), the thrombin substrate, S2238 (Sigma Aldrich, St. Louis, Mo.), was added to the plate. Hydrolysis of this substrate generated a chromogenic substrate detectable at 405 nm. The rate of thrombin generation for each aptamer concentration was determined by use of a thrombin generation standard curve where S2238 was hydrolyzed by known amount of thrombin.

For the Q271 prothrombin substrate, T18.3 and 11HMT were assayed at 14 concentrations from 0 to 1000 nM. The mutant aptamers 18.3Mut1 and 11Mut2 were assayed in seven points over the same concentration range. For the desGlaQ271 substrate, T18.3 was assayed in 14 points from 0 to 30 nM and 11HMT was assayed in 14 points from 0 to 120 nM. The mutant aptamer for each functional aptamer was assayed in seven points over the same range as the functional aptamer.

Light Scattering

Membrane docking of modified FVa was assayed using light scattering was measured at 25° C. with a PTI QuantaMaster fluorescence spectrophotometer (Photon Technology International, Birmingham, N.J.). Vesicles were prepared by sonication to contain a ratio of 75:25 phosphatidylcholine and phosphatidylserine and quantitated using a phosphate assay. Quartz cuvettes with a 0.5 mL volume were washed with HCl and methanol, rinsed with milliQ water, and finally rinsed with 100% methanol before drying with canned air. The outsides of the cuvettes were polished with lint-free cloth. The scattering machine was calibrated with HBS with CaCl2 so the maximum scattering intensity did not exceed 7.75 units. The excitation wavelength was set to 2.0 nm and the excitation slit was 1.1 mm. The emission wavelength was set to 1.2 nm and the emission slit was 1.1 mm. Four cuvettes were utilized for the experimental set up: buffer+PCPS, buffer+200 nM FVa+PCPS, buffer+200 nM FVa+T18.3+PCPS, and buffer+200 nM FVa+18.3Mut1+PCPS. PCPS vesicles were added in 2.0 uM increments to each cuvette using a Hamilton syringe fitted with a repeat pipettor with the assay ranging from 0 to 60 µM. Scattering intensity and errors for each data point were recorded.

Fluorescent Anisotropy

Prothrombinase complex assembly was assayed using fluorescent anisotropy with Alexa-488 FXa at 25° C. with a PTI QuantaMaster fluorescence spectrophotometer (Photon Technology International, Birmingham, N.J.). The machine settings were as follows for slit A: 1.4 mm, 0.93 mm, high volt at 850, gain at 10-3. Slit B was 1.5 nm, high volt at 790, gain at 10-1. All four 0.5 mL quartz cuvettes were utilized in the experimental set up with the following conditions: buffer (HBS with CaCl2)+PCPS, buffer+PCPS+FXa, buffer+PCPS+FXa+T18.3, buffer+PCPS+FXa+18.3Mut1. The final concentrations for PCPS was 10 µM, 100 nM Alexa-488 FXa, 2.0 uM T18.3 or 18.3Mut1, and FVa was assayed from 0-200 nM. Scattering intensity and errors for each data point were recorded.

Results

SELEX Results & Lead Aptamer Selection

Individual aptamer sequences from the FV and FVa selections were determined by DNA sequencing from rounds 8 and 9. For Round 9, 25 sequences from each selection were sent for sequencing. Only sequences which were verified by colony PCR as containing a DNA insert corresponding to the length of the round PCR product were sent for sequencing. For the FVa selection, 23 sequences were resolved well enough for alignment and comparison of their randomized regions. These 23 sequences clustered into two distinct families, where a family was defined as having no more than three nucleotides that differed between the sequences. Initial screening of aptamers yielded zero functional sequences, which prompted re-testing of the Round RNA in a micronized silica stimulated aPTT (FIG. 1).

At this time, Round 8 RNA for the FV selection was also included; however, Round 8 RNA for the FVa selection was not included because there was not enough on hand. Interestingly, it was noted that the anticoagulant activity of Round 8 RNA from the FV selection was much stronger than that of Round 9 (FIG. 1). Given the large difference in activity between rounds, cloning out of Round 8 was initiated for the FV selection. For Round 8, 28 clones were sent out for sequencing and 20 of the resulting sequences were usable for sequence analysis.

At this point, an error in the end of the 3' fixed region was discovered where six nucleotides were mistakenly omitted from the sequence. Discovery of the mistake prompted retesting of all identified sequences to properly include these nucleotides. Rectification of this mistake yielded a variety of aptamers from both selections with anticoagulant activity.

Figure 2:
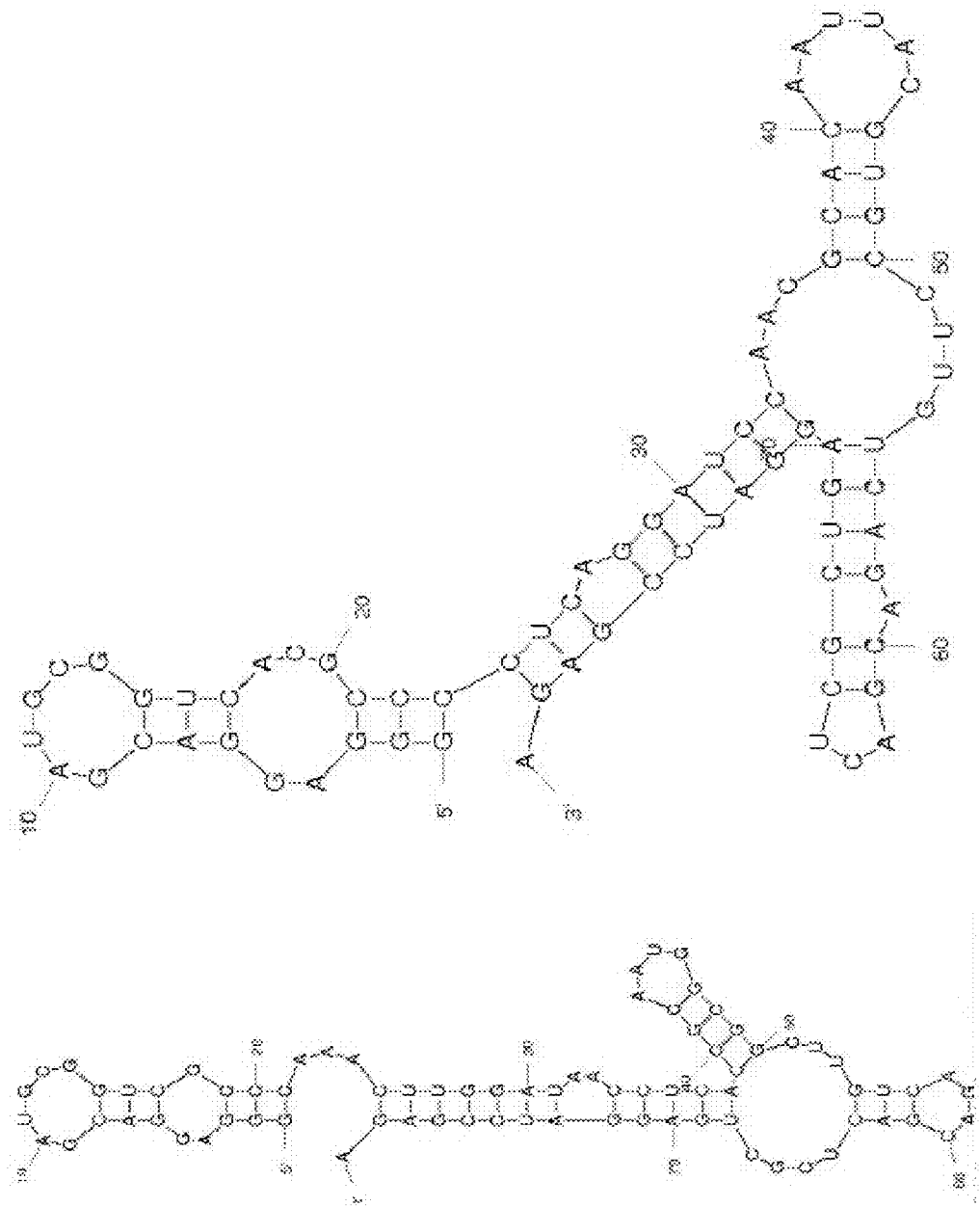
FIG. 2 shows the predicted mFold Structures of Full Length Aptamers. Left: FV R8c7 (SEQ ID NO: 3). Right: FVa R9c11 (SEQ ID NO: 4).

These candidates were screened for activity at a single concentration in an aPTT and binding to both FV and FVa. Based upon performance in both of these assays, a single lead aptamer was chosen from each selection; for the FV selection the lead aptamer was designated FV R8c7 (Round 8 clone 7) and for the FVa selection the lead aptamer was designated FVa R9c11 (Round 9 clone 11) (FIG. 2).

Aptamer Truncation

Reduction of aptamer size to a shorter, functional length is an integral part of aptamer development. The identified lead sequences were 80 nucleotides in length because all sequences from the starting library are this length to allow for the generation of complex shapes. However, portions of these sequences are dispensable without loss of the desired anticoagulant activity. The FVa R9c11 aptamer was reduced to 49 nucleotides directly from the full length of 80 nucleotides (Table 1). A large portion of the aptamer was removed based upon predicted structure similarity to other anticoagulant aptamers. The 5' portion of the predicted mFold structures looked very similar for several aptamers with anticoagulant activity (as seen in FIG. 2). However, the randomized and 3' fixed regions had different structures and each aptamer differed greatly in its ability to anti-coagulate, suggesting the functional portion of the molecule lay in the regions that were structurally dissimilar. This suggested the 5' portion was not contributing to the overall anticoagulant activity of the aptamer. Elimination of this part of the sequence yielded a much smaller aptamer with similar anticoagulant activity. The predicted structure of the truncated aptamer 11HMT can be seen in FIG. 3.

The truncation strategy utilized for FVa R9c11 was not possible with the FV R8c7 aptamer because the attempt yielded an aptamer lacking anticoagulant activity. Because of this, truncation was attempted by reducing stem length in the parent aptamers, with particular emphasis placed on eliminated AU base pairs as they are less stable due to the presence of two hydrogen bonds versus the three present in GC pairs. Mismatched pair and bulge nucleotides were not eliminated in any potential truncates as these bases could have been important for the formation of the aptamer's tertiary structure. Ultimately, none of these truncates had functional anticoagulant activity.

The next truncation strategy utilized antidotes to different portions of the parent aptamer FV R8c7. The antidotes were designed to bind overlapping regions of the parent sequence, preventing it from participating in the overall folded shape of the aptamer. Using this strategy, a portion of the 5' region was identified as being dispensable for aptamer anticoagulant function. The partially truncated aptamer was named T18 and was 60 nucleotides in length. From this shorter truncate, the strategy was switched back to the elimination of AU base pairs. The T18.3 aptamer was designated as the final truncated aptamer generated from R8c7 and was 58 nucleotides in length and used for all further characterization studies (Table 1). The truncated aptamer structures as predicted by mFold can be seen in FIG. 3.

Mutant Aptamer Generation

Figure 4:
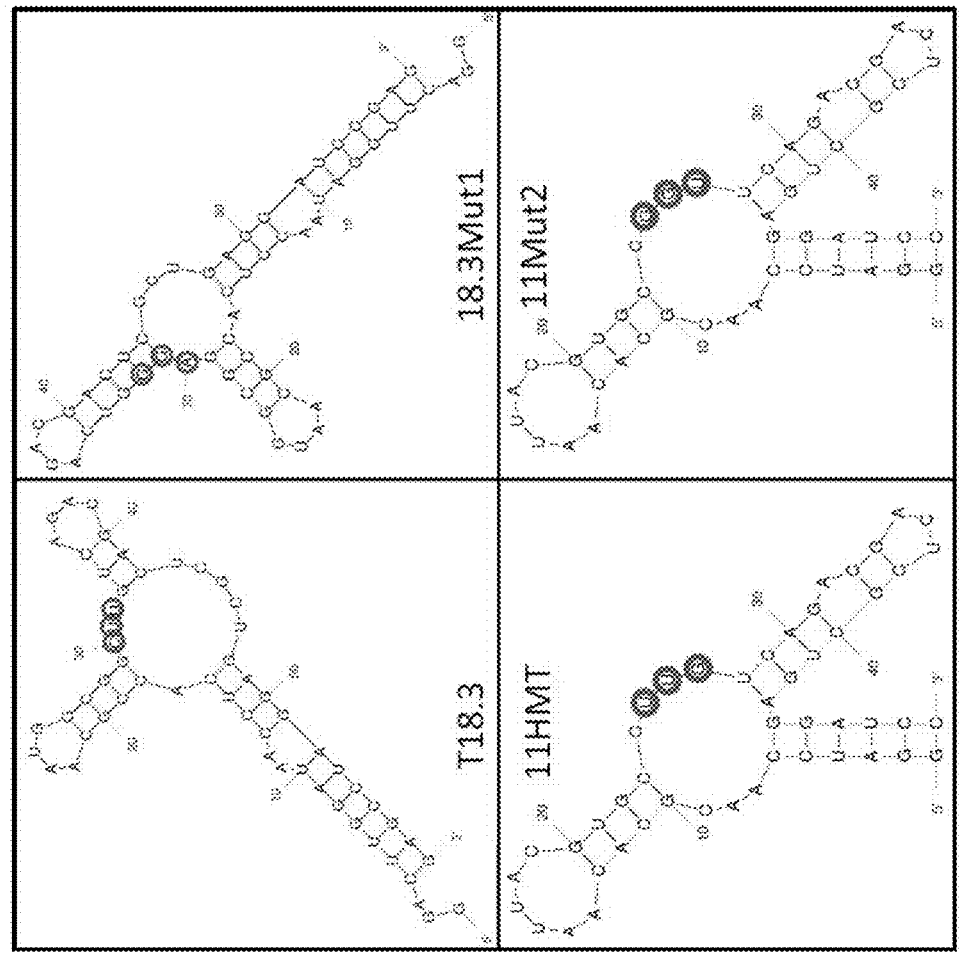
FIG. 4 shows a comparison of mFold Structures of Functional versus Mutant Aptamers. Left: functional aptamers T18.3 (SEQ ID NO: 1) and 11HMT (SEQ ID NO: 2). Right: mutant aptamers—18.3Mut1 (SEQ ID NO: 5) and 11Mut2 (SEQ ID NO: 6).

Once the truncation process was finalized for each selection, mutant aptamers were generated to serve as aptamer-specific controls for further characterization. Two or three mutant aptamers were created by transversion of three nucleotides in the looped regions of each aptamer. Mutation of loop nucleotides was selected as folding of these mutant sequences with mFold generated the same structure or a nearly identical structure as the functional aptamer. Comparison of the mFold structures of the functional and mutant aptamers from each selection can be seen in FIG. 4 and Table 1 contains the sequences of both the functional and mutated truncated aptamers, as well as the full-length parent aptamers.

Binding Affinity to FV and FVa

Binding affinities for 11HMT and T18.3 were obtained using two different assays: double-filter nitrocellulose binding for 11HMT and surface plasmon resonance (SPR) using T18.3. SPR is considered the gold standard for obtaining binding affinities and was only used for T18.3 because complete mechanism of action studies were performed for only this aptamer. However, the double-filter nitrocellulose binding assay does give a good approximation of the binding affinity of an aptamer for its target.

Figure 5:
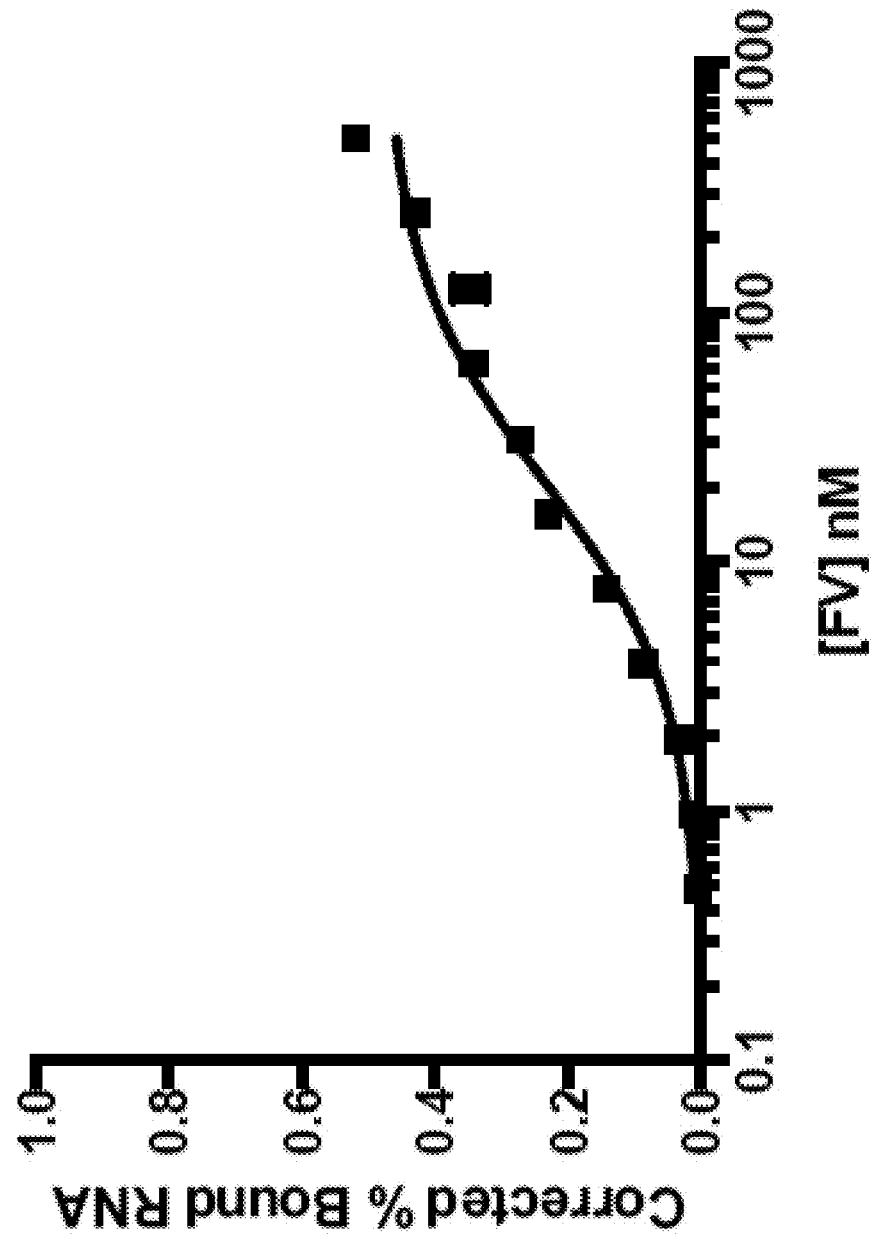
FIG. 5 shows representative Binding Data of 11HMT Binding FV.

Affinity of 11HMT to modified FV and FVa was obtained by screening over a concentration range of 0 to 500 nM for both proteins. In each binding assay, the affinity of 11HMT to each protein was performed in triplicate. Data from three experiments was compiled and analyzed using a one-site specific binding fit in GraphPad Prism 6 and is reported as KD±SEM. The measured apparent KD of 11HMT to FV was 23.16±2.716 nM and 0.8220±0.3569 nM to FVa, indicating a high level of affinity of the aptamer for its target. As seen in FIG. 5, the limitations of this particular binding assay become apparent. The graphed points for the modified FV protein give the appearance of a two-site binding event (a sigmoidal shape followed by another rise after the plateau). This is an artifact of the assay, likely caused by the partitioning step in the assay. While the protein and RNA interact in solution, they are portioned through a membrane sandwich and potentially adopt other conformations while on the membranes. Indeed, we have seen this same two-site binding pattern with other aptamers and their targets, however, we do not have any data suggesting the aptamers are binding in a two-site manner.

Figure 6:
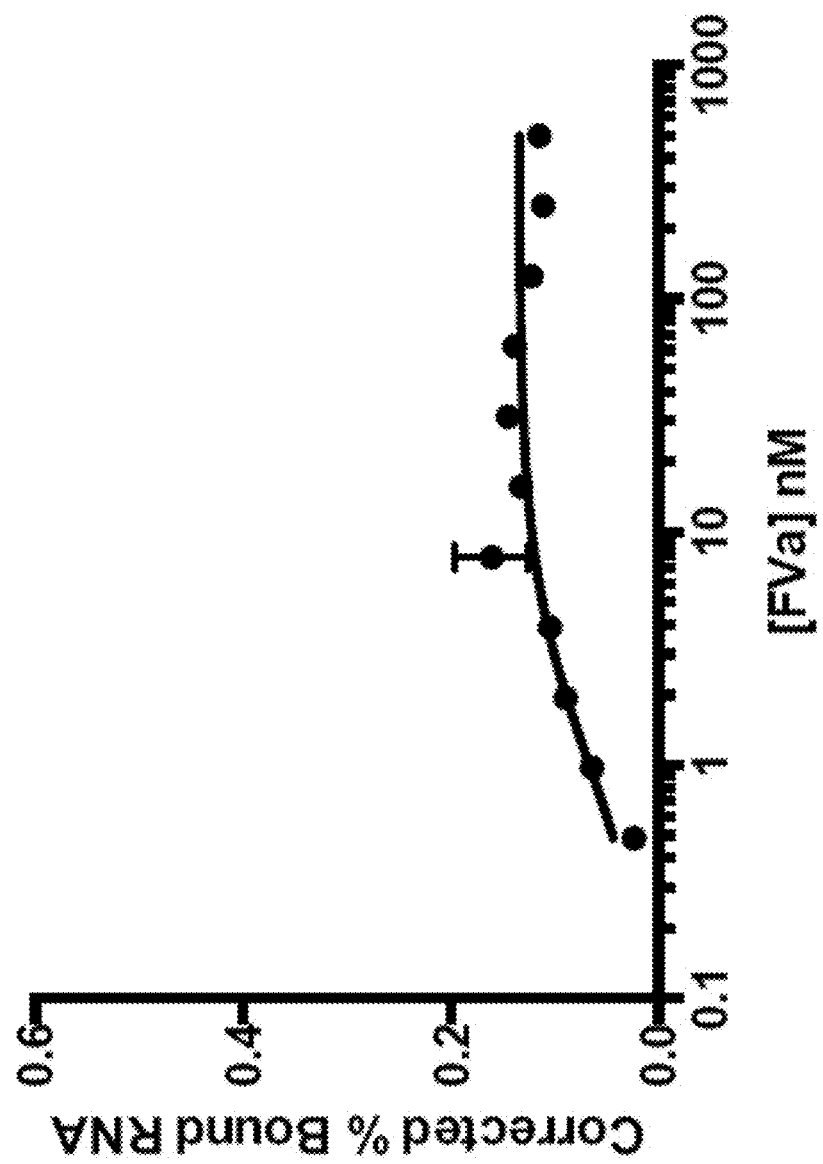
FIG. 6 shows representative Binding Data of 11HMT Binding FVa.

Additionally, in FIG. 6, a poor Bmax (highest achieved percentage of RNA bound) is poor for FVa. While working with this protein, a fair amount of variability in the Bmax was attained across assays, however, reasons for this are unknown. Freezethaw cycles were minimized for the protein and different lots of nitrocellulose and nylon were used over the course of the selections and assays screening affinity of full length clones, potential truncates, and this final truncate. Because the overall percentage of RNA bound is very low, it is likely that this apparent KD is more inaccurate, as evidenced by the greater standard error of the mean, because it is very difficult to generate a sigmoidal shape to be analyzed by the program.

Figure 7:
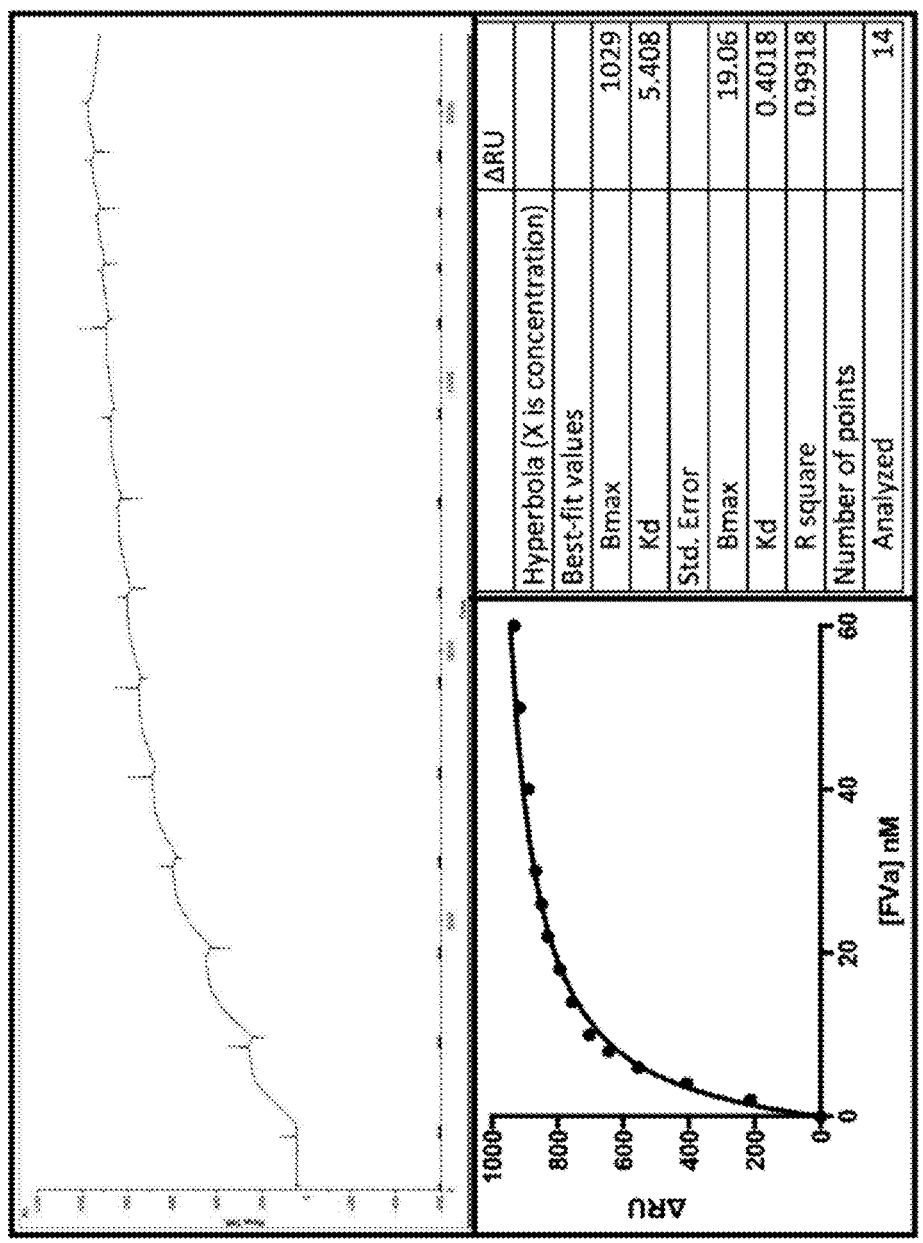
FIG. 7 shows SPR Data to Determine the Affinity of T18.3 for a Protein. Top: Subtraction sensogram from BiaCore 3000. Bottom left: ΔRU versus protein concentration rectangular hyperbola graph. Bottom right: Abbreviated data analysis table generated by Prism 6.

Affinity of T18.3 was assessed using the BiaCore 3000 and SPR rather than the nitrocellulose-based binding assay. In addition to measuring the affinity to FV and FVa, affinity towards the light and heavy chains of FV was assessed. The heavy and light chains were purified. The apparent KD for each protein was determined by flowing increasing concentrations of each protein over the aptamer on the chip. The RUs four seconds before the end of each protein injection was captured and converted to a ΔRU value using the buffer injection at the beginning of the experiment. The ΔRU value was graphed versus protein concentration to generate a rectangular hyperbola. This curve was fitted in Prism 6 to determine the apparent KD for each protein. FIG. 7 shows the subtraction sensogram (top panel), the ΔRU versus protein concentration graph (lower left), and an abbreviated data analysis table generated by Prism 6.

The apparent KD of T18.3 for FV and FVa, as seen in Table 3, was quite good, with the affinity for FVa being approximately 6 nM and 10 nM for FV. T18.3 was able to bind the light chain of FV with a KD of approximately 5 nM, making it very similar to the affinities of FV and FVa. The affinity towards the heavy chain of the protein was significantly lower with the KD being somewhere between 60 and 100 nM, approximately an order of magnitude weaker than the affinity for all other FV-related proteins assayed.

TABLE 3

Binding Affinities of T18.3 for FV derivatives

| Protein | Run | $K_D$ (nM) | Std Dev | R Square |
|---|---|---|---|---|
| FV | 1 | 16.55 | 1.665 | 0.9872 |
|  | 2 | 10.00 | 0.9592 | 0.9875 |
|  | 3 | 8.213 | 1.12 | 0.9758 |
| FVa | 1 | 6.222 | 0.4668 | 0.9918 |
|  | 2 | 5.408 | 0.4018 | 0.9918 |
|  | 3 | 5.115 | 0.3720 | 0.9921 |
| Heavy Chain | 1 | 105.1 | 8.054 | 0.9958 |
|  | 2 | 59.46 | 5.909 | 0.9937 |
|  | 3 | 57.77 | 4.371 | 0.9960 |
| Light Chain | 1 | 1.926 | 0.1596 | 0.9880 |
|  | 2 | 1.504 | 0.1560 | 0.9816 |
|  | 3 | 7.997 | 0.8176 | 0.9865 |

Target Specificity

Figure 8:
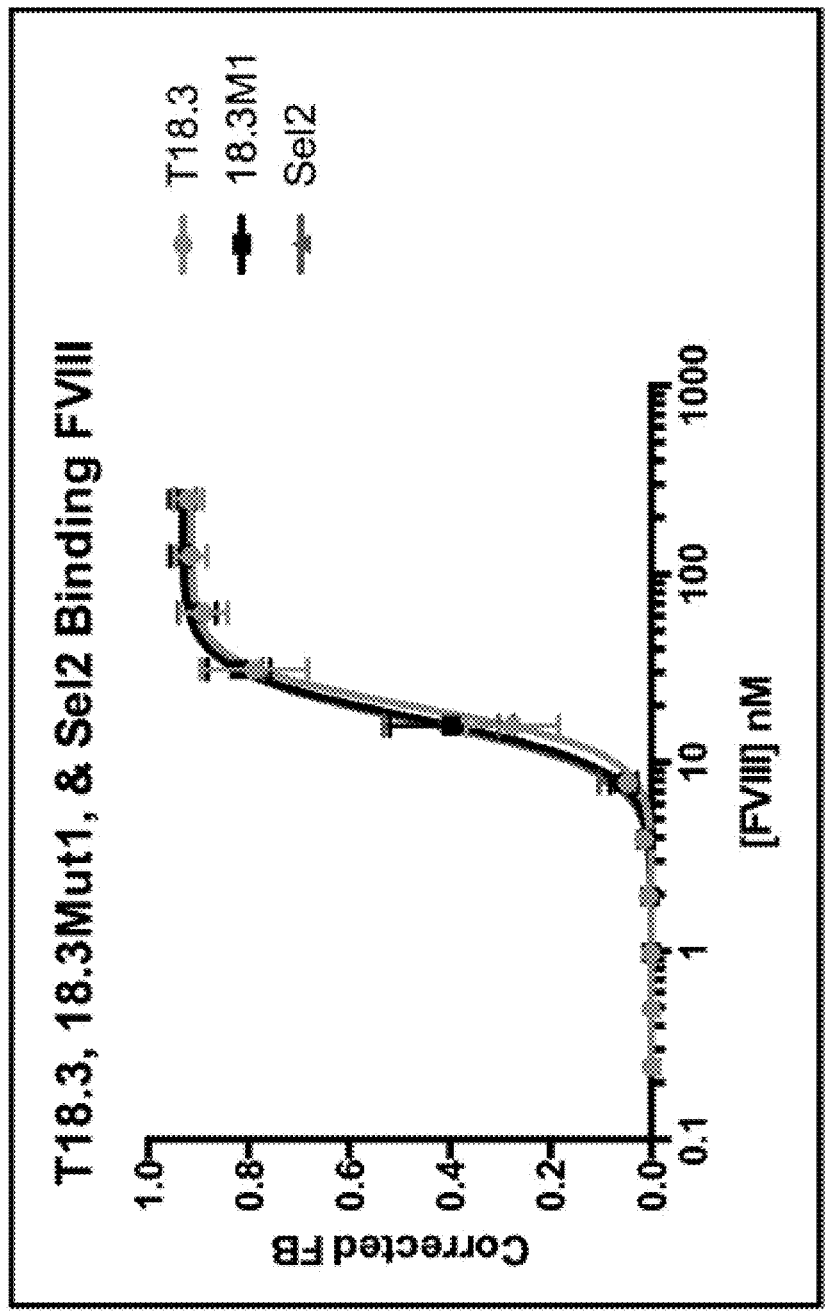
FIG. 8 shows representative Binding Data of T18.3, 18.3Mut1, and Sel2 Binding FVIII.

Unlike many of the other coagulation proteins, FV is not directly homologous to any other proteins that participate in hemostasis. FV does share domain arrangement homology with FVIII; both proteins are set up in the following fashion: A1-A2-B-A3-C1-C2. However, these two genes did not arise from a gene duplication event, indicating the homology between the two proteins is restricted to their domain arrangement. Because only T18.3 was taken forward for complete characterization of the mechanism of anticoagulation, only this aptamer and mutant were screened for interaction with FVIII. Other work indicated that the FVIII protein exhibits a high affinity towards all types of RNA. Because of this observation, affinity of T18.3, 18.3Mut1, and Sel2 (the starting library for this aptamer) was assessed using nitrocellulose-based binding assays. Radiolabeled T18.3, 18.3Mut1, and Sel2 were assessed for binding to FVIII over a protein range of 0-250 nM. All RNAs were able to bind to FVIII as seen in FIG. 8. The Sel2 RNA was included as an important control in this experiment; both T18.3 and 18.3Mut1 bound to FVIII with an apparent KD within 3.0 nM of Sel2. This indicated that the binding of both T18.3 and 18.3Mut1 was not productive.

Because the FV aptamers bound in a similar fashion as the starting library, we concluded that their binding is merely a function of the sticky nature of FVIII rather than specific binding resulting in inhibitory activity. Though FIG. 8 shows non-specific binding of T18.3, as well as two other aptamers, to FVIII, we are confident that it is specific only to FV and FVa based upon our experience with the specificity of the other aptamers generated by our lab.

Figure 9:
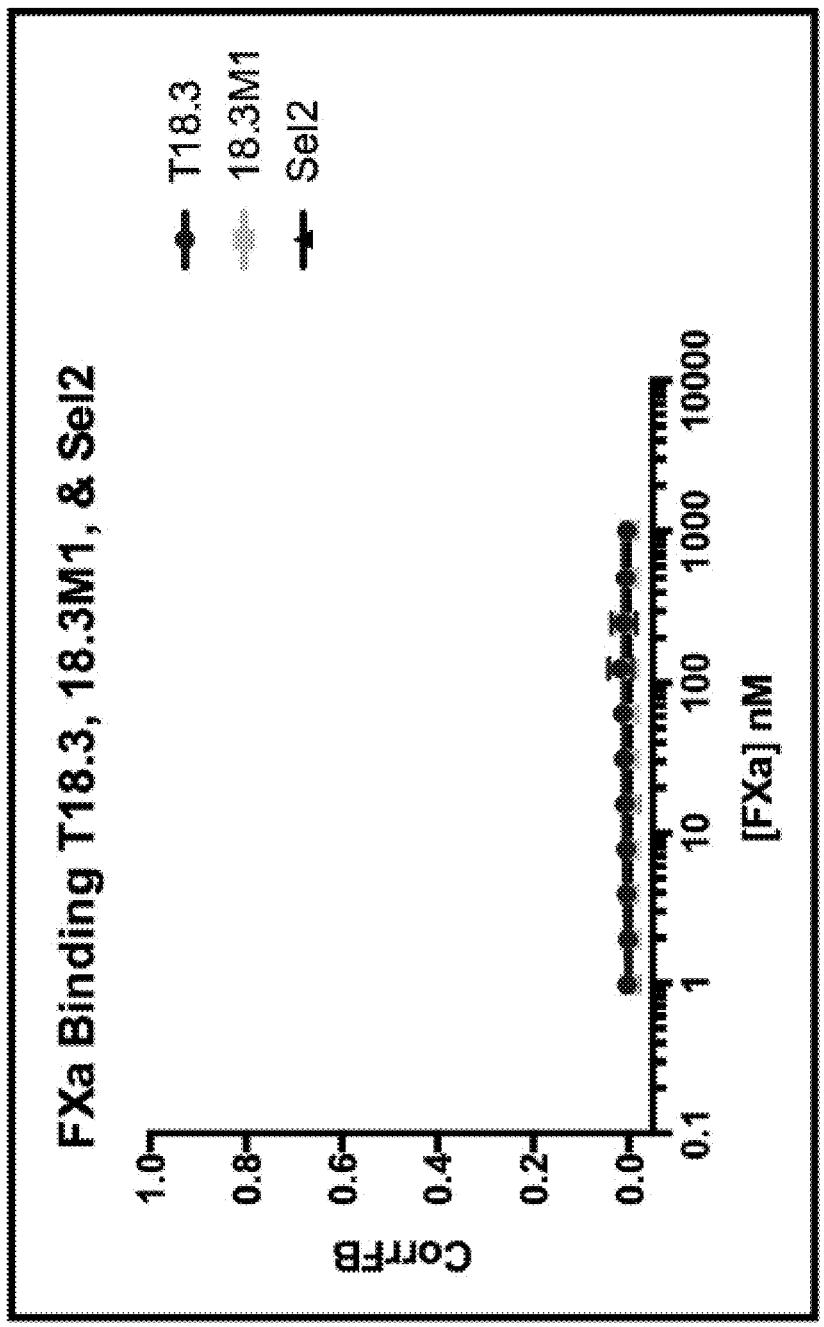
FIG. 9 shows T18.3, 18.3Mut1, and Sel2 Binding to FXa.

The other protein screened in the aptamer specificity process was FXa. Because FXa and FVa form the prothrombinase complex, questions about the ability of the FV aptamers to interact FXa are raised. T18.3, 18.3Mut1, and Sel2 were screened for binding to human FXa from 0-1000 nM (FIG. 9). None of the three RNAs were able to bind to FXa at even the highest concentration testing, indicating that T18.3 binding was specific to the FV and FVa proteins and that FXa did not exhibit the "stickiness" that was characteristic of FVIII.

Aptamer Competition

Using the truncated aptamers binding site location was assessed using a competition nitrocellulose-binding assay. Both T18.3 and 11HMT were radiolabeled with $^{32}$P as described for the other nitrocellulose binding assays. FV protein concentration was fixed at the binding affinity of each aptamer for FV (15 nM for T18.3 and 20 nM for 11HMT). Cold RNA was serially diluted starting at a 64-fold excess of cold RNA down to 1/64th the binding affinity concentration. Cold 11HMT was able to compete with hot T18.3 for binding to FV. Additionally, the reciprocal is also true. Cold T18.3 was able to compete with hot 11HMT for binding to FV (FIG. 10). Competition for binding between the two aptamers indicates their binding epitopes on FV are identical or share significant overlap.

Plasma-Based Coagulation Assays

Figure 11:
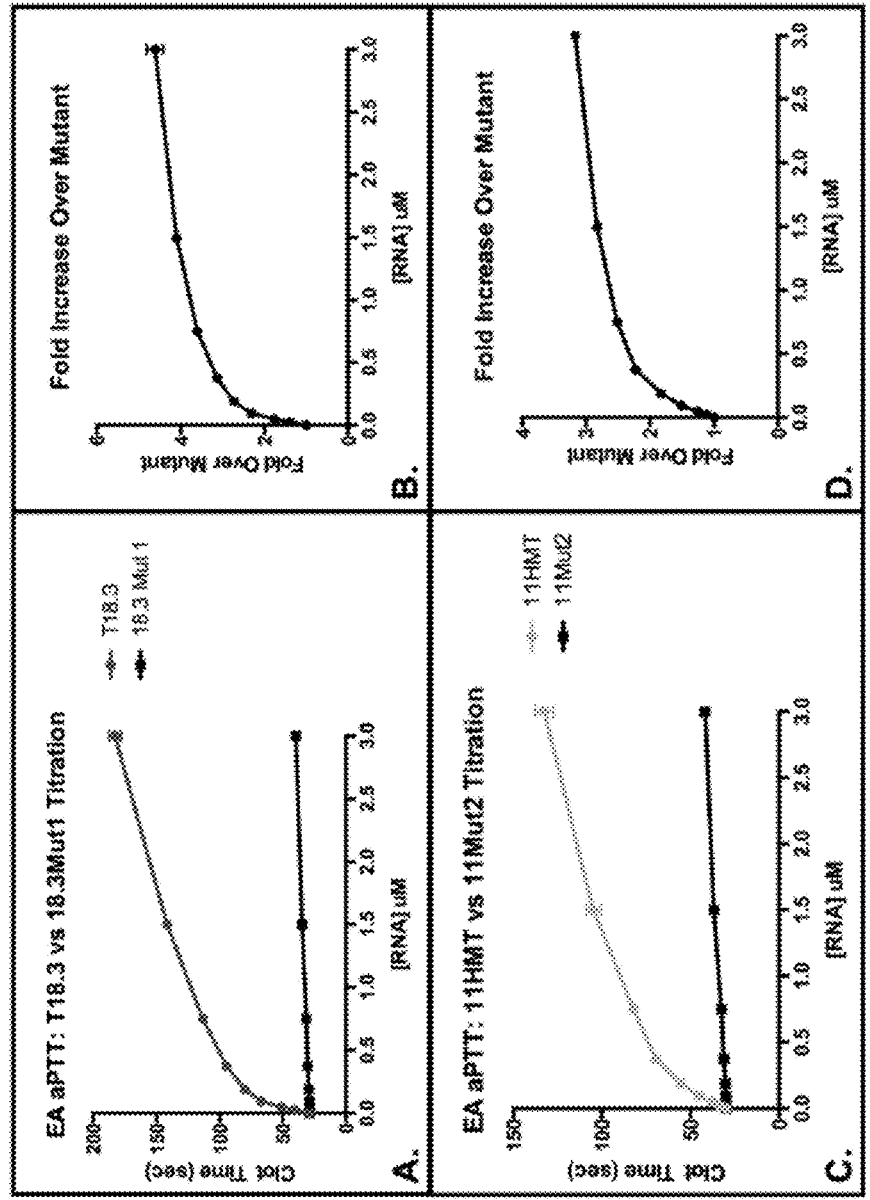
FIG. 11 shows Ellagic Acid Stimulated aPTT Titration of T18.3 and 11HMT.

Because FV is located in the common pathway of coagulation, both the aPTT and PT assays were used to assess the ability of each aptamer to extend clotting time beyond normal. Using an ellagic acid stimulator in the aPTT, both aptamers were able to dose dependently increase clotting time relative to their mutant (FIG. 11). The FV deficient donor utilized by George King Biomedical has an aPTT clot time that ranges from 90-120 seconds. Both aptamers were able to achieve this level of anticoagulation, however higher concentrations of 11HMT were necessary to reach this range. The slightly increased clot time observed for both mutants was a result of the non-specific anticoagulant effect of a large amount of RNA and not a result of any anticoagulant effect of the mutant aptamers themselves. By normalizing the clot time extension to fold over mutant activity, it was possible to observe a leveling off of aptamer activity (FIGS. 11B and 11D).

In the PT assay, like in the aPTT, both aptamers dose-dependently increased clotting time, but in a less robust manner. The maximum achievable increase over mutant activity was two-fold, rather than the four-fold increase observed in the aPTT (FIG. 12). This observation likely stemmed from the difference in pathway activation; the PT is stimulated with tissue factor derived from rabbit brain and is much stronger than the stimulus in the aPTT. This is demonstrated by the differences in normal clotting time; 10-12 seconds for the PT and 28-34 seconds for the aPTT. While the effect was not as dramatic in the PT, both functional aptamers showed an increase in clotting time relative to their mutants.

Figure 13:
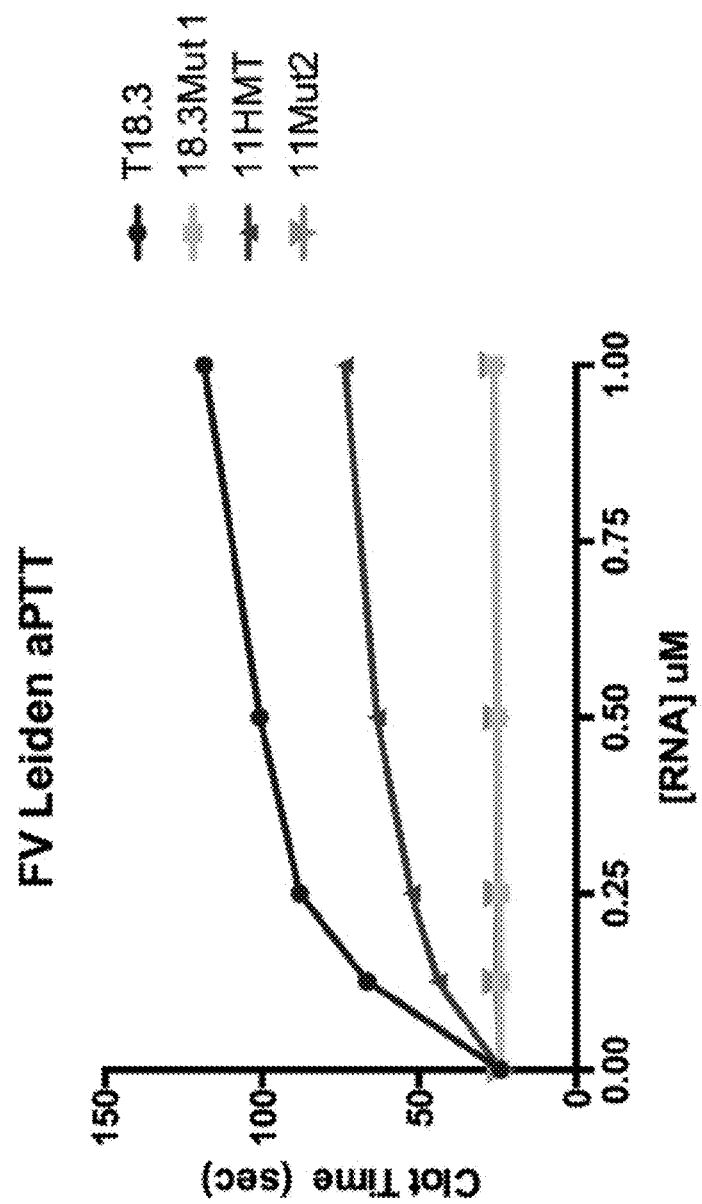
FIG. 13 shows Ellagic Acid Stimulated aPTT with Congenital FV Leiden Plasma.

The most common mutation in the FV protein results in the thrombophilic condition known as FV Leiden. Using platelet poor plasma from a donor with the FV Leiden mutation, T18.3 and 11HMT were assayed for the ability to extend clot time relative to their point mutants. Both aptamers were able to bind the FV Leiden plasma and extend the clot time in a dose dependent manner (FIG. 13). This indicates either aptamer would be functional in patients with this mutation and would be appropriate for use in all patients.

Whole Blood and Plasma Thromboelastography

While both aptamers had strong anticoagulant activity in plasma-based coagulometer assays, platelet-poor plasma lacks an important part of the hemostatic system: platelets. This is particularly important when characterizing these FV/FVa targeting aptamers because platelets are another source of FV. Whole blood thromboelastography assays (TEGs) allows for assaying aptamer activity against both sources of FV.

The first dose of each aptamer and mutant tested was 300 nM; this dose was selected because it was ten-fold higher than the circulating concentration of FV and should inhibit nearly all of the FV and FVa present in the whole blood. Surprisingly, neither aptamer had any effect on the lag time (time to clot formation, normal lag time=2-8 minutes) relative to the mutant aptamers or the buffer control (FIG. 14, panels A, D, G, and H). Using blood from the same donor, the dose was then increased to 1.0 µM, thirty-fold higher than the circulating concentration of FV. Again, there was no difference in lag time relative to the mutant aptamers (FIG. 14, panels E, F, I, and J). To ensure this was a true observation and not a donor specific effect, the same experiment was performed using another blood donor. This experiment confirmed that neither 300 nM nor 1.0 µM of either aptamer was able to extend the lag time (data not shown). This observation potentially suggested that the aptamers were unable to bind to platelet derived FV, so TEG experiments with both platelet-rich and platelet-poor plasma were carried out.

Figures 15A, 15B, 15C, 15D:
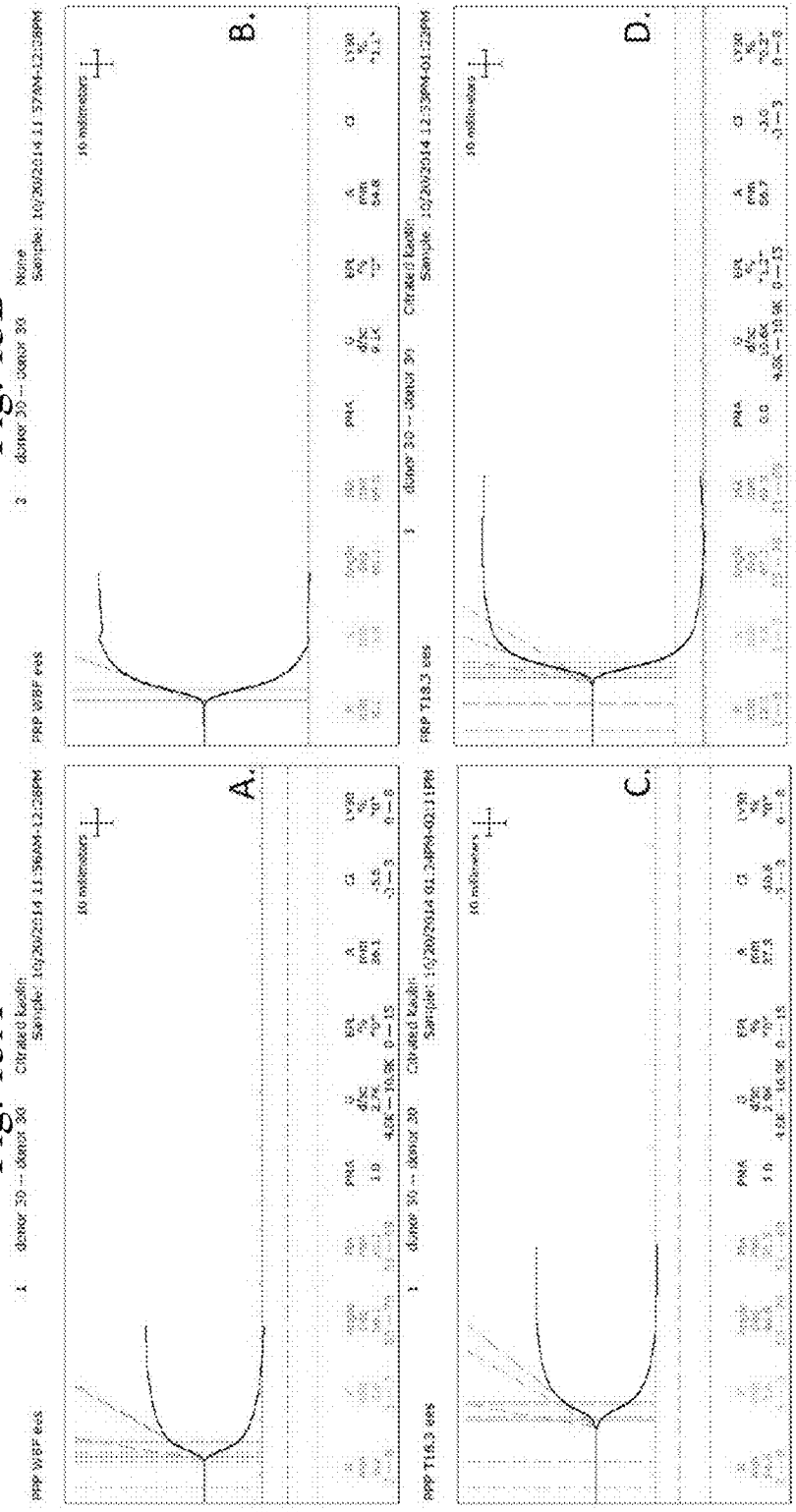
FIG. 15A shows PPP buffer control.
FIG. 15B shows PRP buffer control.
FIG. 15C shows PPP with 1.0 μM T18.3.
FIG. 15D shows PRP with 1.0 μM T18.3.
Figure 15E:
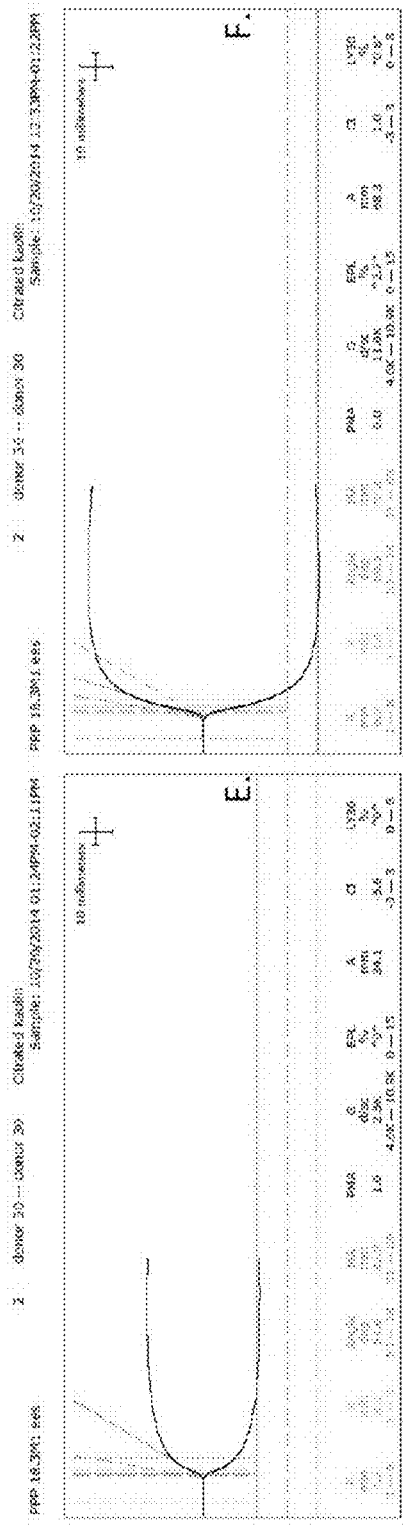
FIG. 15E shows PPP with 1.0 μM 18.3Mut1.
Figure 15F:
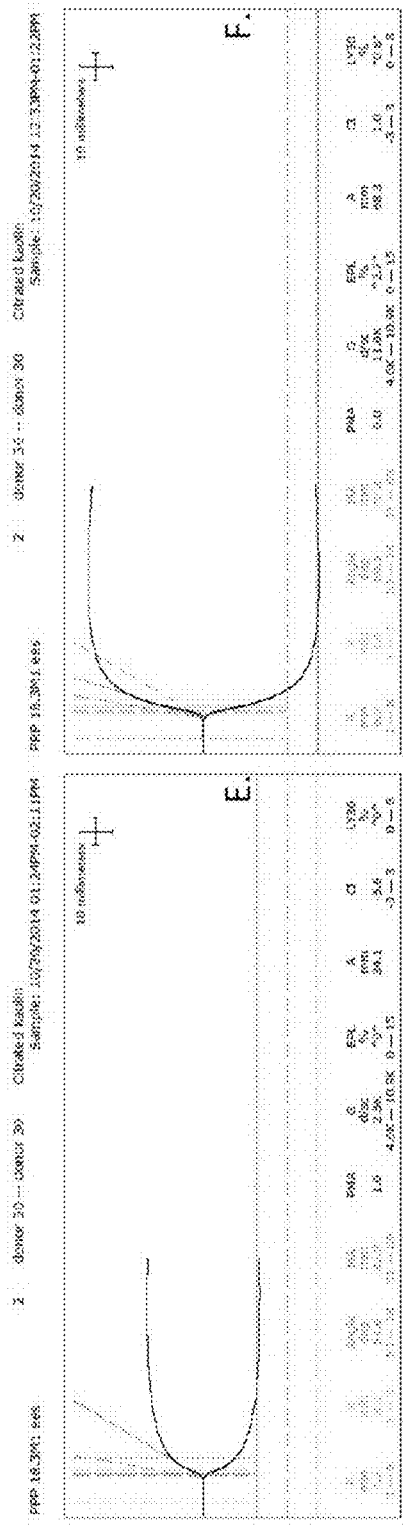
FIG. 15F shows PRP with 1.0 μM 18.3Mut1.

In platelet-poor plasma, T18.3 at 1.0 µM was able to increase the lag time to 14.8 minutes, which was outside the normal range and approximately two-fold longer than the buffer control and mutant lag times (FIG. 15, panels A, C, and E). In platelet-rich plasma, the same amount of T18.3 increased the lag time to 12.2 minutes, which was just slightly outside the normal range and was just less than a two-fold increase relative to mutant and buffer controls (FIGS. 15B, D, and F).

Figure 16:
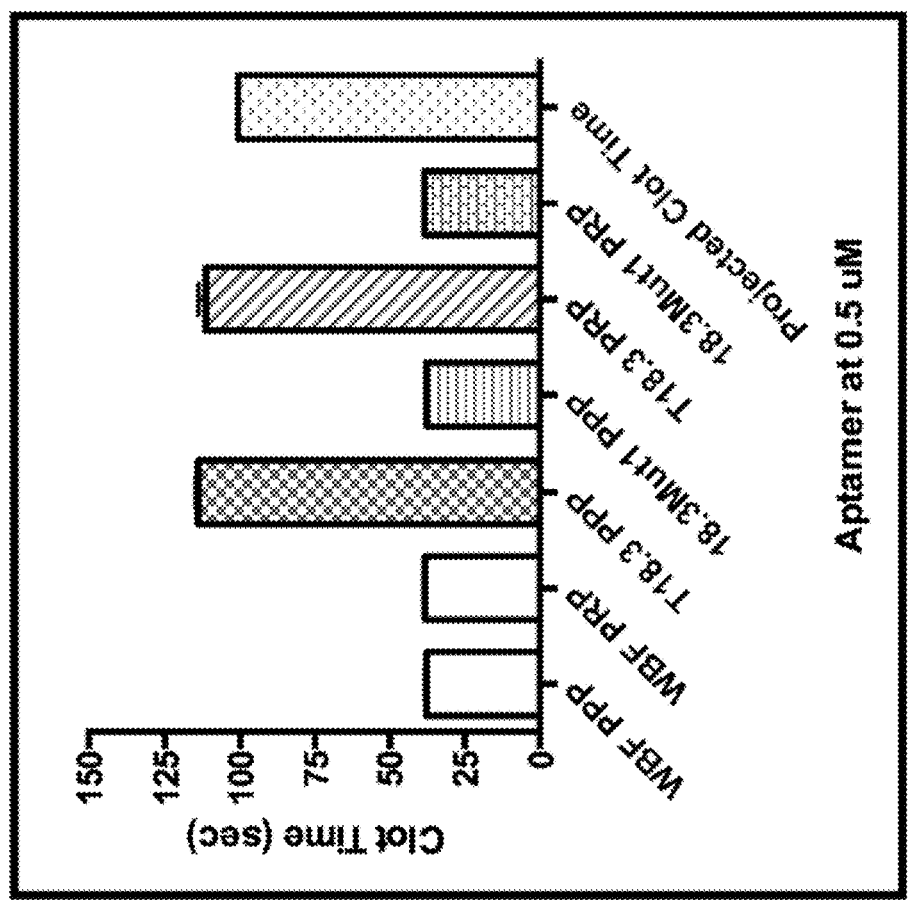
FIG. 16 shows T18.3 Anticoagulation of PPP and PRP in an aPTT. T18.3 and 18.3Mut1 at 0.5 μM in PPP and PRP. Projected clot time estimated from titration curve of T18.3.

Using the same platelet-rich and platelet-poor plasma, a single dose (0.5 µM) aPTT assay was run to compare clotting times. Clot time extension was in good agreement with the same dose of T18.3 in pooled platelet-poor plasma and the values obtained from the platelet-rich and platelet-poor plasmas were within a few seconds of each other (FIG. 16). The data obtained from the plasma-based TEG experiments and the aPTT experiment indicated that T18.3 was able to anticoagulate platelet-derived FV. However, this did not explain the lack of lag time extension observed when whole blood was used.

To see if the differences between functional and mutant aptamer could be distinguished better by reducing the amount of clot stimulating agent, the kaolin activator was diluted to 75% strength and the PPP and PRP TEGs were repeated. This dilution pushed the buffer control lag time 0.2 minutes outside the normal range (8.2 minutes), but the difference in lag time for PPP and PRP were essentially the same as the experiment with full strength activator (data not shown). Again, an aPTT was run at a single concentration in both PPP and PRP to compare anticoagulant ability, and the results were the same as the previous experiment with no observable difference in aptamer functionality between the two types of plasma (data not shown).

One final whole blood thromboelastography experiment was attempted and included a five minute incubation of the aptamer with whole blood at 37° C., prior to the addition of kaolin activator and $CaCl_2$. T18.3 was tested at 1.0 and 2.5 µM to see if a further increase in concentration would have any effect on the lag time. The lag time of the 1.0 and 2.5 µM doses were 14.0 and 14.4 minutes, respectively, compared to 6.6 and 5.8 minute lag times of the mutant aptamer at the respective doses. Given the inability of T18.3 to extend beyond the 11-14 minute lag time threshold, it appeared that the aptamer was unable to inhibit all of the FV and FVa present in the sample. Using a combination of FV deficient and pooled normal plasma, 100%, 99%, and 95% FV deficient plasma samples were prepared and tested in a TEG. Surprisingly, both the 100% and 99% FV deficient assays were unable to clot during the entire 180 minute experiment (data not shown). The 95% FV deficient assay had a lag time of 17.8 minutes, very close to the previously observed maximum lag time extension achieved by the aptamers in whole blood. This data suggested that a minimum of 95% of the available FV/FVa needed to be bound by the aptamer in order to achieve even a modest increase in the lag time of this assay. However, given that the 2.5 µM dose had a lag time that was only 0.4 minutes longer than the 1.0 µM dose, this suggested that incrementally higher doses of the aptamer could only negligibly increase the lag time and a dose grossly higher would be needed to achieve greater than 95% inhibition. Because the dose required to show an extension of lag time would be prohibitively and unreasonably high, this particular assay was not pursued further as a tool to demonstrate the anticoagulant effect of T18.3 and 11HMT.

Aptamer Reversal

A major benefit of the aptamer class of therapeutics is the ability to reverse their functional activity. One method of reversal takes advantage of their RNA composition; oligonucleotide antidotes can be designed based upon the aptamer's sequence and bind the aptamer through Watson-Crick base-pairing. For T18.3 and 11HMT, antidotes were designed to run the length of the aptamer with a new antidote starting five nucleotides closer to the 3' end than the previous antidote. All antidotes were 18 nucleotides long, which has been shown to be long enough to abrogate aptamer function without potentially forming a stable structure on its own. Antidote functionality was assayed using an ellagic acid stimulated aPTT by adding a third incubation step prior to the initiation of clotting. Antidotes were screened at a three-fold excess relative to the aptamer concentration. Interestingly, none of the oligonucleotide antidotes were able to reverse the anticoagulant activity of the T18.3 aptamer (data not shown). To ensure the antidotes had the ability to reverse the aptamer, the aptamer and antidote were melted together by heating to 95° C. for 3 minutes and allowed to cool to ambient temperature for 3 minutes. When melted together, all antidotes were able to fully reverse the activity of T18.3 (data not shown). When the aptamer and antidote were melted and folded separately, but allowed to pre-incubate at room temperature prior to addition to the plasma, only some were able to partially reverse aptamer activity, while others were completely unable to reverse aptamer function (data not shown). This indicated that the inability of antidotes to reverse the aptamer once it bound to FV and FVa was likely due to a combination of the aptamer's tertiary structure and the affinity of the aptamer for its target.

The 11HMT aptamer was screened for an antidote using the same overlapping strategy as T18.3. The screen revealed one antidote that was able to partially abrogate the aptamer's function. Increasing the antidote to aptamer ratio did not result in more complete reversal of the aptamer's activity. The inability to reverse either aptamer with the oligonucleotide strategy was a new observation for our lab. All previous aptamers the lab has developed were able to be reversed using this particular method. The lack of success with this method could be attributed to two factors: the aptamer's tertiary structure, or the antidote could not access the aptamer due to complex binding interactions between the aptamer and the cofactor.

Figure 17:
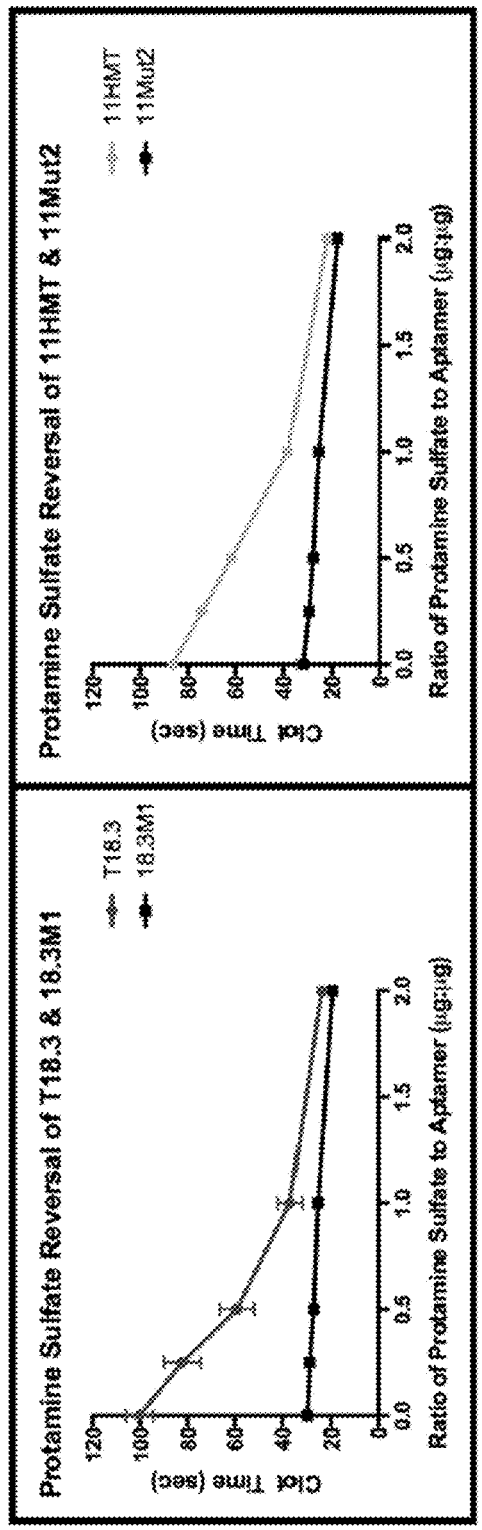
FIG. 17 shows Protamine Sulfate Reversal of T18.3 and 11HMT. Left: T18.3 versus 18.3Mut1 reversal. Right: 11HMT versus 11Mut2 reversal.

Despite the fact that the oligonucleotide antidotes were unsuccessful, our lab has also described another method for aptamer reversal that takes advantage of the overall negative charge of the aptamer. This strategy was termed a "universal antidote" because these antidotes worked on any aptamer sequence, rather than being sequence specific and involves using a cationic polymer. A commonly administered drug that is a cationic protein is protamine sulfate, which is used as a reversal agent for heparin anticoagulation. This protein was screened for use as a universal antidote for both aptamers because it is already used in patients. Using the protamine sulfate, the anticoagulant activity both aptamers was reversed (FIG. 17).

Reversal was graphed in a µg to µg amount of protamine sulfate to aptamer because protamine sulfate is somewhat size dispersed making molarity calculations inaccurate. Somewhat unsurprisingly, it took more than 1 µg of protamine sulfate to reverse 1 µg of aptamer because protamine sulfate is approximately 5 kDa, whereas the aptamers are approximately 19 kDa (T18.3) and 16 kDa (11HMT). Ultimately, aptamer activity could be completely reversed at higher ratios of protamine sulfate to aptamer and anticoagulant activity of the aptamers could be "tuned" by addition of less protamine sulfate. The protamine sulfate was also observed to slightly shorten the clot time when added in increasing amounts to the mutant aptamers. However, the slight reduction in clot time was small enough that it would not be cause for concern in a patient.

Cross Reactivity with Other Species

Figure 18A:
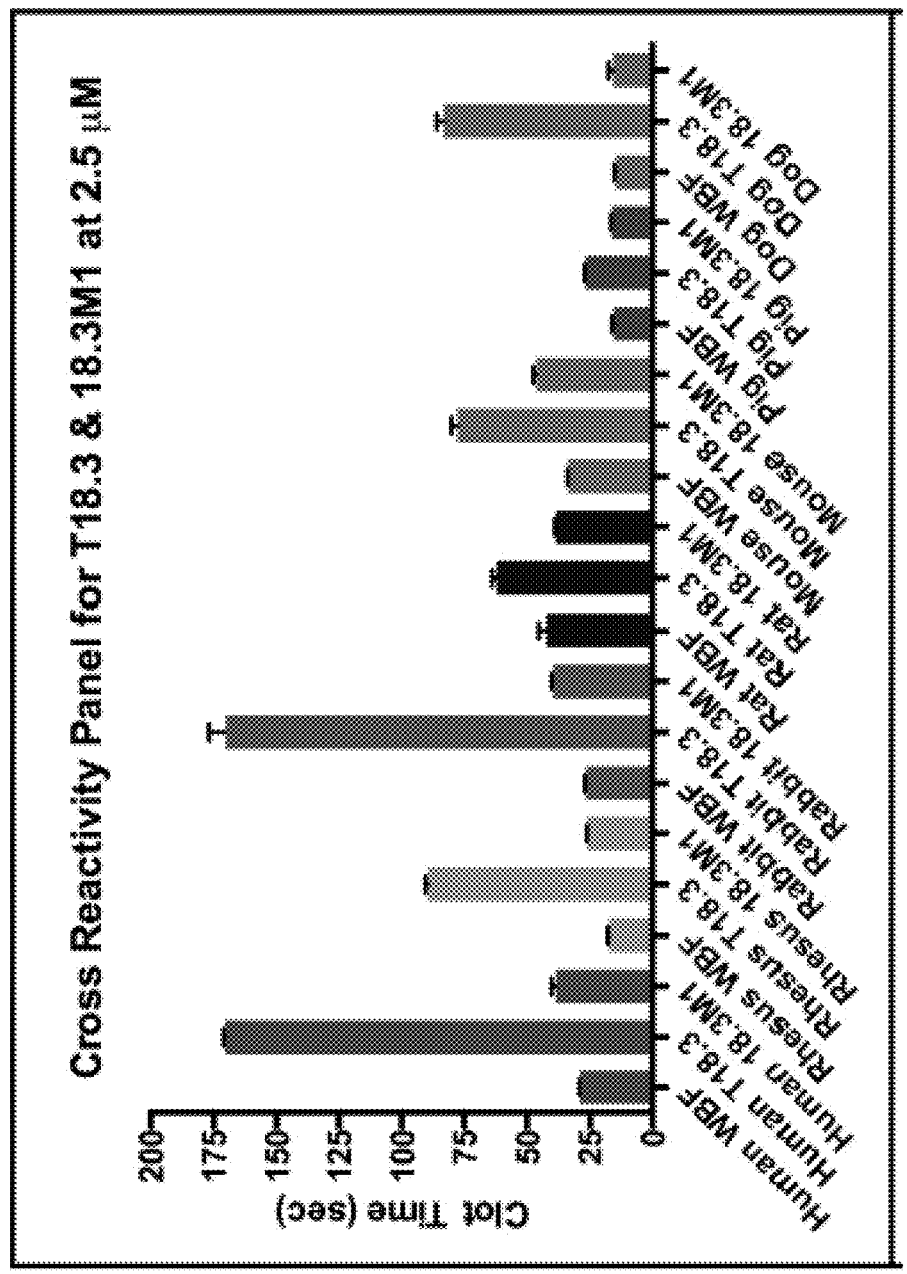
FIG. 18A: Clot time in presence of T18.3 or its corresponding mutant in the indicated sample.
Figure 18B:
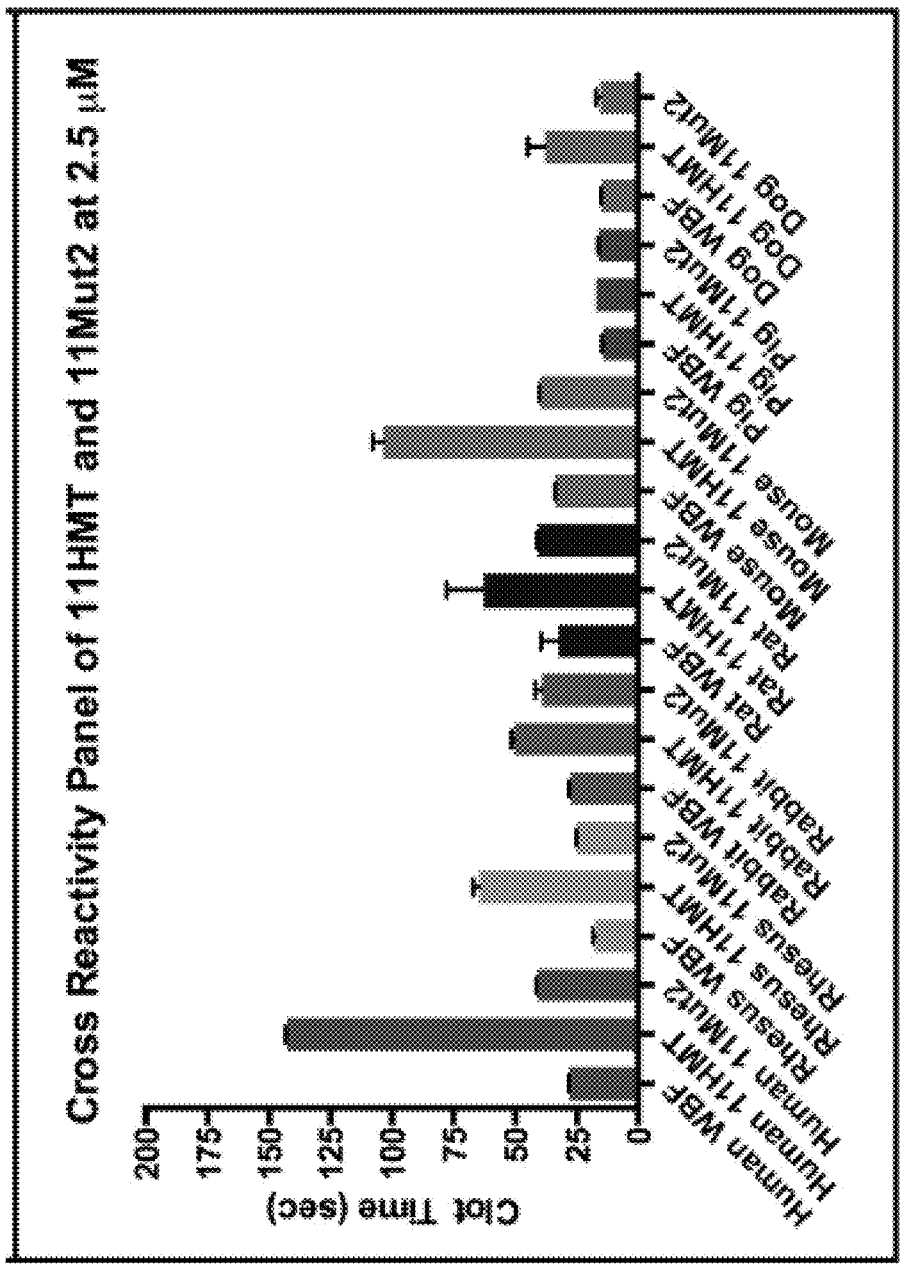
FIG. 18B: Clot time in the presence of 11HMT or its corresponding mutant in the indicated sample. Colors represent the same species in both graphs.

Both T18.3 and 11HMT were generated using modified forms of human FV and FVa. However in order to move the aptamers forward as potential anticoagulants, we must determine which preclinical animal models are compatible with the aptamers. Based on previous experience in the lab, cross-reactivity of a specific aptamer with the target protein from another species cannot be predicted with protein homology. To determine if the aptamers could bind to the FV/FVa of any other species, we utilized the ellagic acid-stimulated aPTT using a much higher dose of aptamer than generally used in human plasma. This increased dose would allow us to observe even modest cross-reactivity in another species, which is influenced by affinity to the alternate protein and any differences in plasma concentration relative to human plasma. Pooled mixed gender plasmas from various species were used in this assay to best mimic the pooled normal human plasma used in the aPTT and PT assays. FIG. 18 shows the results of the crossreactivity panels for each aptamer. Interestingly, the cross-reactivity was not identical for T18.3 and 11HMT (FIG. 18A and FIG. 18B). The biggest difference in cross-reactivity of the two aptamers was with rabbit plasma. T18.3 showed very strong anticoagulation of rabbit plasma at 2.5 µM with a clot time of approximately 160 seconds, which was nearly indistinguishable from the anticoagulation level achieved in human plasma at the same concentration. However, 11HMT was only able to extend the clot time to approximately 50 seconds, only ten seconds longer than the mutant aptamer at the same concentration. Additionally, T18.3 worked better in canine plasma, extending clot time to approximately 75 seconds versus approximately 40 seconds for 11HMT. In murine plasma, 11HMT was the superior anticoagulant over T18.3, achieving a clot of time approximately 100 seconds versus 75 seconds, respectively. The mutant aptamers extended clotting time to approximately 43 seconds. These differences could be explained by the slightly different sizes of each aptamer (58 versus 49 nucleotides). Given their different sizes and likely different tertiary structures, it is possible that the aptamers bury slightly different surfaces on the FV and FVa proteins. The area buried by T18.3 made it a better anticoagulant to the rabbit forms of the protein, whereas 11HMT was more successful with murine FV and FVa. Both aptamers showed good activity in rhesus plasma, moderate activity in rat plasma, and neither aptamer worked in swine plasma. This cross-reactivity information allows us to select appropriate models for any animal studies that may be undertaken.

Generation of Meizothrombin in a Purified System

Inhibition of FV and FVa function should result in an overall reduction in thrombin generation by the prothrombinase complex. Using a thrombin chromogenic substrate that is cleavable by an α-thrombin precursor, we were able to assess the amount of thrombin generated by the prothrombinase complex in the presence of T18.3 and 11HMT. We utilized prothrombin variants that could generate only meizothrombin, rather than wild-type prothrombin, to eliminate having α-thrombin and meizothrombin present in the assay with the ability to hydrolyze the thrombin chromogenic substrate, S2238.

The first prothrombin variant tested was a Q271 prothrombin, where the arginine at position 271 was mutated to a glutamine so cleavage could only occur at the arginine 320. This prothrombin variant was membrane dependent similar to wild-type prothrombin and needs to be membrane-bound in order to be cleaved by the prothrombinase complex. Using a purified protein system containing HBS with 5 mM $CaCl_2$, FVa, either T18.3 or 11HMT, phospholipid surfaces, the Q271 variant, and initiated with FXa, meizothrombin generation was measured over a range of aptamer concentrations, 0-1000 nM. Both aptamers showed a marked decrease in the rate of thrombin generation as the aptamer concentration increased (FIG. 19).

Figure 19:
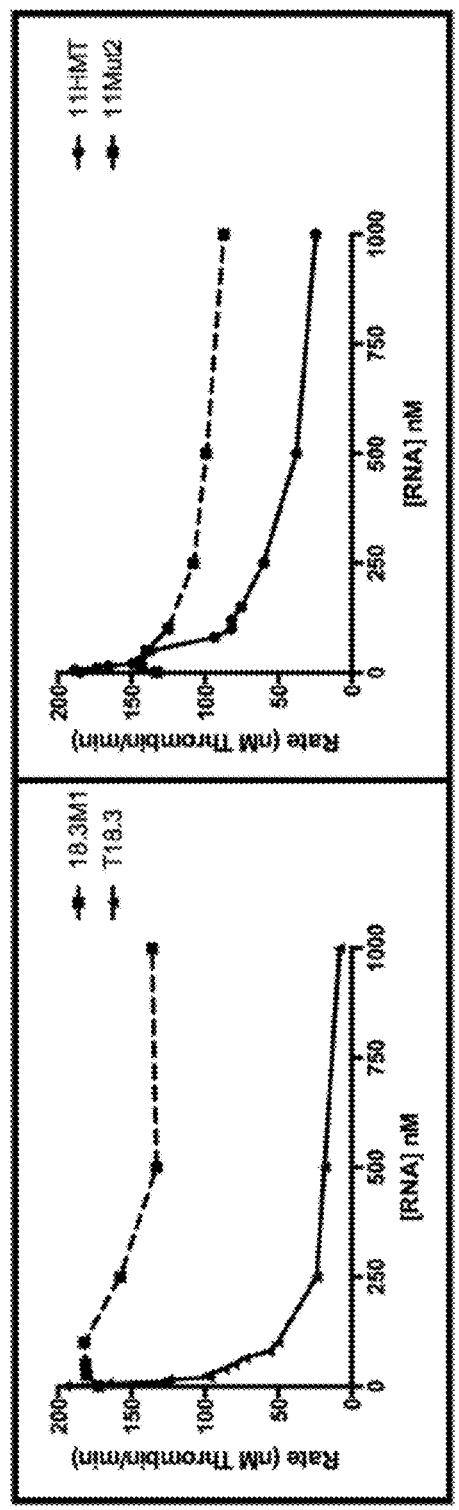
FIG. 19 shows the Rate of Thrombin Generation from Q271 Prothrombin Substrate. Left: T18.3 and 18.3Mut1. Right: 11HMT and 11Mut2.

Neither mutant aptamer was able to significantly reduce meizothrombin generation over the same concentration range (FIG. 19). Additionally, the presence of the aptamers did not alter the hydrolysis of the chromogenic substrate by meizothrombin, suggesting the reduction in meizothrombin generation was a result of FVa inactivity rather than a disruption of chromogenic substrate cleavage (data not shown). The overall reduction in the rate of meizothrombin generation was more pronounced with the T18.3 aptamer than the 11HMT aptamer, indicating that T18.3 had better inhibitory effects on FVa.

Figure 20:
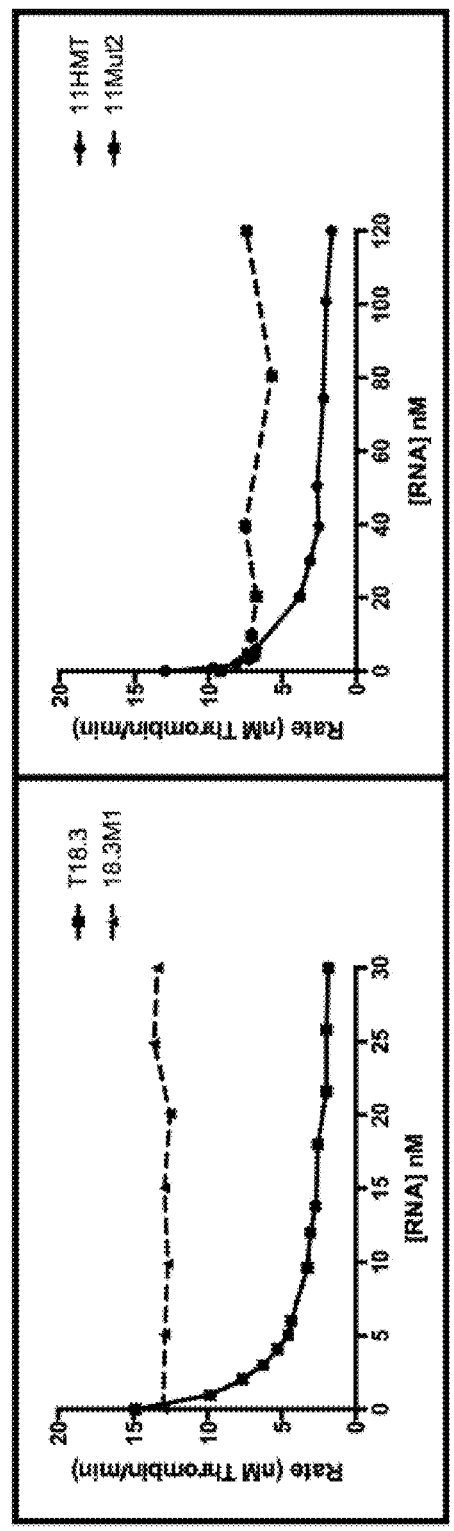
FIG. 20 shows the Rate of Thrombin Generation from desGla Q271 Prothrombin Substrate. Left: T18.3 and 18.3Mut1. Right: 11HMT and 11Mut2.

A second prothrombin variant was also used to screen for meizothrombin generation: a desGlaQ271. This prothrombin variant carried the same arginine to glutamine mutation as the previous variant, but lacked the membrane docking dependence due to the removal of the Gla domain. Again, both aptamers were able to reduce meizothrombin generation with T18.3 showing superior inhibitory activity (FIG. 20). T18.3 was able to greatly reduce meizothrombin generation over the 0-40 nM range, whereas 11HMT had to be screened over a range from 1-120 nM to achieve the same level of inhibition (FIG. 20). It was verified that the aptamer did not alter the ability of this prothrombin variant to cleave the chromogenic substrate and no alterations in hydrolysis were observed (data not shown). Computer modeling suggested the aptamers may have been functioning as competitive inhibitors of prothrombin binding to FVa. This modeling data was utilized to direct later experiments to determine the mechanism of action.

Prothrombinase Complex Assembly FRET Studies

Prothrombinase complex assembly with its substrate prothrombin can be assayed using fluorescent resonance energy transfer (FRET) with specifically labeled proteins.

The first pair of labeled proteins included Alexa488-FXa in the FXa active site as the donor, and prothrombin with an Alexa532 on the 271 cleavage site that was attached by mutating the arginine to a cysteine. If the complex did not assemble, or the donor was not able to interact with prothrombin in its usual manner, transfer between the fluorophores would be lost. When either 2.5 or 4.5 μM of the T18.3 aptamer was added to the system, there was no change in the percentage of emission (buffer=62.0%, 2.5 μM T18.3=65.4%, and 4.5 μM T18.3=64.9%). As a negative control, 10 mM EDTA was added and the emission percentage dropped to 3.95% as was expected since FVa, FXa, and prothrombin all require Ca++ to fold correctly.

The second FRET pair of proteins assayed was FVa with Alexa488 on the 539 residue paired with the Alexa532 prothrombin. This pair of proteins directly probed the interaction between prothrombin and FVa. When 2.5 μM T18.3 was added to this FRET pair, no changes in emission percentage were observed relative to the buffer control (17.5% with T18.3, 16.3% with buffer). This indicated FVa was still able to interact with prothrombin and disproved the earlier hypothesis about the aptamer blocking the FVa prothrombin interaction as the mechanism of action.

Membrane Docking of FVa

Figure 21:
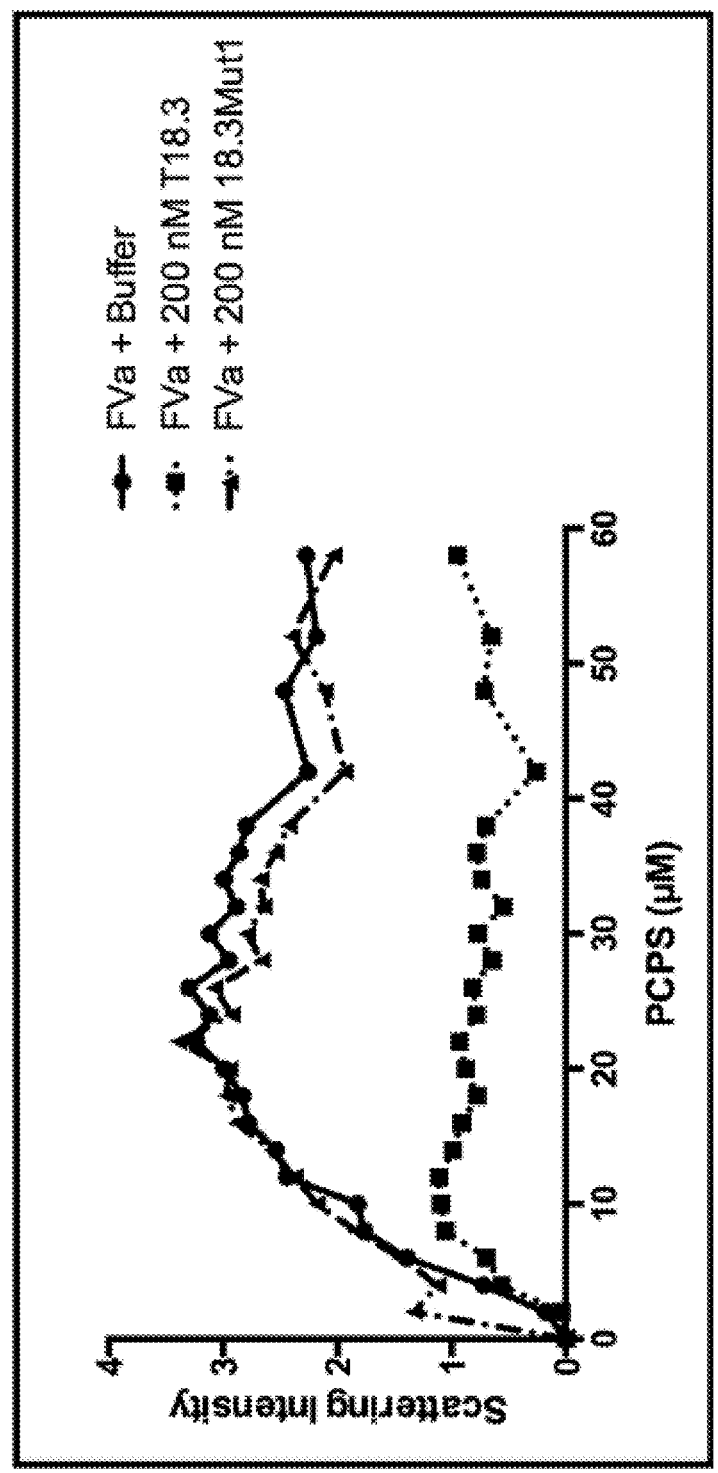
FIG. 21 shows Light Scattering of FVa Docking to PCPS Vesicles.

While showing a reduction in the generation of thrombin and its precursors was important, it did not give any indication of the aptamers mechanism of inhibition. Because T18.3 was the more potent inhibitor of the two aptamers that were developed, further mechanistic studies were carried out with only this aptamer and its corresponding mutant. One of the potential mechanisms of this aptamer was blocking the interaction of FVa with membrane surfaces. Human FVa requires docking to membranes in order to assemble into the prothrombinase complex (FXa and FVa dock separately and then come together to form the complex). Without membrane docking of FVa, complex assembly does not occur. Using a light scattering assay, the ability of T18.3 to abrogate FVa membrane binding was probed. As seen in FIG. 21, in the presence of T18.3, FVa showed delayed and reduced binding to phospholipid surfaces as the concentration of membranes was increased. In contrast, the mutant aptamer did not alter membrane binding of FVa and that curve was superimposable on the buffer control curve (FIG. 21). Screening of the full-length parent aptamer, FV R8c7, at 2.0 μM showed a robust ability to inhibit the interaction of FVa with phospholipid surfaces, indicating the potency of the aptamer was not significantly reduced during the truncation process and the mechanism of action appeared to remain the same (data not shown). Given the robust ability of T18.3 to block the FVa-membrane interaction, this was identified as the primary mechanism through which T18.3 derived its anticoagulant activity.

Prothrombinase Complex Assembly

Because T18.3 strongly prevented FVa from interacting with phospholipid surfaces, a consequence of this would be abrogation of prothrombinase complex assembly. Unlike the FRET experiments discussed above, fluorescence anisotropy was used to interrogate complex assembly. The only fluorescently labeled protein in this set up was FXa, tagged with Alexa488. During assay optimization, we discovered that the aptamer interacted with the Oregon Green label on the OG488-FXa and prevented the fluorophore from responding to complex assembly. However, the Alexa488-FXa emission was not altered by the aptamer making it suitable for use in this assay.

Figure 22:
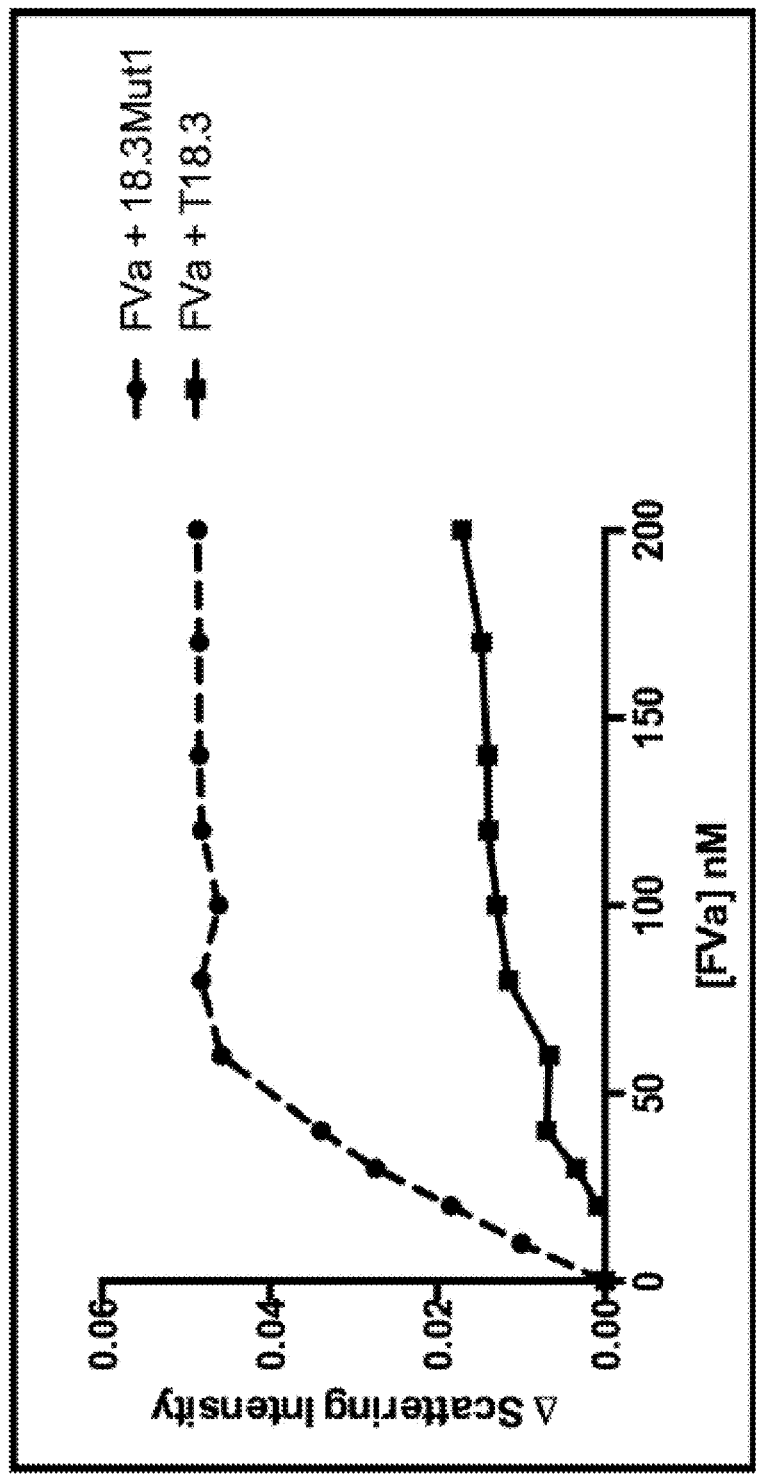
FIG. 22 shows Fluorescent Anisotropy of Prothrombinase Complex Assembly in the Presence of 2.0 μM of T18.3 and 18.3Mut1.

In this assay, FXa, phospholipid surfaces, and T18.3 or 18.3Mut1 were added to the cuvette and allowed to interact. Increasing amounts of FVa preincubated with buffer, T18.3, or 18.3Mut1 was added to each cuvette and changes the anisotropy readings were recorded. Because such a small volume of FVa was being added, the overall concentration of aptamer in the cuvette changed negligibly over the course of the experiment. FVa concentrations assayed from 0-200 nM protein. The presence of T18.3 delayed complex assembly and reduced the overall amount of complex that was able to assemble, while 18.3Mut1 and buffer did not alter complex assembly (FIG. 22 and data not shown). This result confirmed that by blocking the membrane interaction of FVa, T18.3 disrupts prothrombinase complex assembly.

Discussion

The results show that it is possible to develop an anticoagulant aptamer targeting coagulation cascade cofactor FV/FVa. The mechanism of the T18.3 aptamer is derived from its ability to abrogate FVa docking to membrane surfaces and, consequently, disrupt prothrombinase complex assembly. However, this aptamer can be controlled by administration of protamine sulfate, making it a directly reversible anticoagulant.

We claim:

1. An aptamer comprising
    SEQ ID NO: 1,
    SEQ ID NO: 2,
    a polynucleotide having at least 85% sequence identity to SEQ ID NO: 1,
    a polynucleotide having at least 85% sequence identity to SEQ ID NO: 2,
    a polynucleotide comprising from 5' to 3' the nucleotide sequence GGA, a first stem forming region consisting of 7 nucleotides, a first loop region consisting of the nucleotide sequence AA, a second stem forming region consisting of 4 nucleotides, a second loop region consisting of the nucleotide sequence A, a third stem forming region consisting of 4 nucleotides, a third loop region consisting of the nucleotide sequence AAUG, a fourth stem forming region consisting of 4 nucleotides and capable of forming a stem with the third stem forming region, a fourth loop region consisting of the nucleotide sequence CUU, a fifth stem forming region consisting of 3 nucleotides, a fifth loop region consisting of the nucleotide sequence AGAC, a sixth stem forming region consisting of 3 nucleotides and capable of forming a stem with the fifth stem forming region, a sixth loop region consisting of the nucleotide sequence UCGCU, a seventh stem forming region consisting of 4 nucleotides and capable of forming a stem with the second stem forming region, an eighth stem forming region consisting of 7 nucleotides and capable of forming a stem with the first stem forming region, or
    a polynucleotide comprising from 5' to 3' a first stem forming region consisting of 6 nucleotides, a first loop region consisting of the nucleotide sequence AAC, a second stem forming region consisting of 4 nucleotides, a second loop region consisting of the nucleotide sequence AAUUAC, a third stem forming region consisting of 4 nucleotides and capable of forming a stem with the second stem forming region, a third loop region consisting of the nucleotide sequence CUUG, a fourth stem forming region consisting of 4 nucleotides, a fourth loop region consisting of the nucleotide sequence A, a fifth stem forming region consisting of 2 nucleotides, a fifth loop region consisting of the nucleotide sequence ACU, a sixth stem forming region consisting of 2 nucleotides and capable of forming a stem with the fifth stem forming region, a seventh stem forming region consisting of 4 nucleotides and capable of forming a stem with the fourth stem forming region, and an eighth stem forming region consisting of 6 nucleotides and capable of forming a stem with the first stem forming region.

2. The aptamer of claim 1, wherein the aptamer comprises SEQ ID NO: 3, SEQ ID NO: 4, a polynucleotide having at least 85% sequence identity to SEQ ID NO: 3, or a polynucleotide having at least 85% sequence identity to SEQ ID NO: 4.

3. The aptamer of claim 1, wherein the aptamer binds to Factor V or Factor Va.

4. The aptamer of claim 1, wherein the polynucleotide is an RNA polynucleotide.

5. The aptamer of claim 1, wherein the polynucleotide comprises at least one nucleotide base modification selected from the group consisting of a 2'fluoro modification, a 2'O-methyl modification, a 5' modification, and a 3'modification.

6. The aptamer of claim 1, wherein the polynucleotide comprises a 5' linker and/or a 3' linker.

7. The aptamer of claim 1, wherein the polynucleotide further comprises a stability agent.

8. The aptamer of claim 7, wherein the stability agent is selected from the group consisting of polyethylene glycol (PEG), cholesterol, albumin, and Elastin-like polypeptide.

9. The aptamer of claim 8, wherein the stability agent is linked to the 5' end of the polynucleotide.

10. The aptamer of claim 8, wherein the polynucleotide and the stability agent are linked by a covalent bond.

11. The aptamer of claim 8, wherein the polynucleotide and the stability agent are linked by a tag system.

12. The aptamer of claim 11, wherein the tag system is selected from the group consisting of biotin/streptavidin, and biotin/NeutrAvidin.

13. A dimer, trimer, or tetramer comprising the aptamer of claim 1.

14. An antidote comprising a polynucleotide having a nucleotide sequence reverse complementary to and capable of hybridizing to at least 8 nucleotides of the aptamer of claim 1.

15. A pharmaceutical composition comprising a pharmaceutical carrier and the aptamer of claim 1.

16. A method for preventing blood clot formation in a subject comprising administering to the subject the aptamer of claim 1 in a therapeutically effective amount to prevent blood clot formation in the subject.

17. The method of claim 16, wherein the subject suffers from FV Leiden, atrial fibrillation or is at risk of having a Deep Vein Thrombosis, a stroke, a heart attack, or a pulmonary embolism.

18. The method of claim 16, further comprising administering to the subject an antidote in a therapeutically effective amount to neutralize the aptamer.

19. The method of claim 18, wherein the antidote comprises the antidote of claim 14.

20. The method of claim 16, wherein the subject is a human.

* * * * *